US011917959B2

(12) United States Patent
Ovadya et al.

(10) Patent No.: US 11,917,959 B2
(45) Date of Patent: Mar. 5, 2024

(54) MULTI-EAR SYSTEM TO ENHANCE MONOCOT PLANT YIELD

(71) Applicant: Monsanto Technology LLC, St. Louis, MO (US)

(72) Inventors: Daniel Ovadya, St. Louis, MO (US); Beth Savidge, St. Louis, MO (US); Kyle Smith, St. Louis, MO (US); Dale Val, St. Louis, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 16/995,391

(22) Filed: Aug. 17, 2020

(65) Prior Publication Data

US 2020/0375129 A1 Dec. 3, 2020

Related U.S. Application Data

(63) Continuation of application No. 15/745,224, filed as application No. PCT/US2016/042608 on Jul. 15, 2016, now Pat. No. 10,772,274.

(60) Provisional application No. 62/193,389, filed on Jul. 16, 2015.

(51) Int. Cl.
| | | |
|---|---|---|
| *A01H 3/04* | (2006.01) |
| *A01H 1/06* | (2006.01) |
| *A01H 5/10* | (2018.01) |
| *A01H 6/46* | (2018.01) |
| *A01N 43/84* | (2006.01) |
| *A01H 1/08* | (2006.01) |

(52) U.S. Cl.
CPC ............. *A01H 3/04* (2013.01); *A01H 1/06* (2013.01); *A01H 5/10* (2013.01); *A01H 6/4684* (2018.05); *A01N 43/84* (2013.01); *A01H 1/08* (2013.01); *A01H 6/4678* (2018.05)

(58) Field of Classification Search
CPC ........................................................ A01H 4/00
See application file for complete search history.

(56) References Cited

U.S. PATENT DOCUMENTS

| | | |
|---|---|---|
| 4,243,405 A | 1/1981 | Balasubramanyan et al. |
| 4,435,203 A | 3/1984 | Funaki et al. |
| 5,866,513 A | 2/1999 | Michelotti et al. |
| 7,902,437 B1 | 3/2011 | Carrigan |
| 8,791,047 B2 | 7/2014 | Haas et al. |
| 10,561,083 B2 | 2/2020 | Feng et al. |
| 2010/0050501 A1 | 3/2010 | Rooney et al. |
| 2010/0169999 A1 | 7/2010 | Cui et al. |
| 2013/0205438 A1 | 8/2013 | Barton et al. |
| 2013/0303372 A1 | 11/2013 | Haas et al. |
| 2014/0266196 A1 | 9/2014 | Dai et al. |
| 2014/0310832 A1 | 10/2014 | McIntyre et al. |

FOREIGN PATENT DOCUMENTS

| | | |
|---|---|---|
| CN | 1622752 A | 6/2005 |
| CN | 1843089 A | 10/2006 |
| CN | 102118965 A | 7/2011 |
| CN | 102273460 A | 12/2011 |
| CN | 103260393 A | 8/2013 |
| EP | 0753257 A1 | 1/1997 |
| WO | 03056903 A2 | 7/2003 |
| WO | 2007038075 A1 | 4/2007 |
| WO | 2014/037947 A1 | 3/2014 |
| WO | 2015/168659 A1 | 11/2015 |
| WO | 2017011737 A1 | 1/2017 |

OTHER PUBLICATIONS

Schluttenhofer et al 2011 Industrial Crops and Products 33:720-726 (Year: 2011).*
Xu et al 2004 Plant Growth and Regulation 44:231-241 (Year: 2004).*
Bayat et al., "Paclobutrazol and Salicylic Acid Application Ameliorates the Negative Effect of Water Stress on Growth and Yield of Maize Plants", Journal of Research in Agricultural Science, 2012, pp. 127-139, vol. 8, No. 2.
Chalyk et al., "Regular Segregation of Four Recessive Marker Genes Among Maternal Haploids in Maize," Plant Breeding, 2000, pp. 363-364, vol. 119.
Chalyk, "Properties of Maternal Haploid Maize Plants and Potential Application to Maize Breeding," Euphytica, 1994, pp. 13-18, vol. 19.
Chen et al., "Micron traditional Chinese medicine—Study and application of ultrafine powder of traditiona Chinese medicine", China Medical Science and Tech Press, 1st edition, p. 155, Aug. 31, 2007.
Coe, "A Line of Maize With High Haploid Frequency," The American Naturalist, 1959, pp. 381-382, vol. 93, Issue 873.
Deimling et al., "Methodology and Genetics of In Vivo Haploid Induction in Maize," Vort. Pflanzenzuchtg, 1997, pp. 203-224, vol. 38.
English Translation of Office Action and Search Report for CN Application 2016800460661, dated Mar. 3, 2020.
Espindula et al., "Use of Growth Retardants in Wheat", Plant Daninha, 2009, vol. 27, No. 2, pp. 379-387.
Geiger et al., "Doubled Haploids in Hybrid Maize Breeding", Maydica, 2009, pp. 485-499, vol. 54.
Gomez et al., "Can Yield Potential be Increased by Manipulation of Reproductive Partitioning in Quinoa (Chenopodium Quinoa)? Evidence from Gibberellic Acid Synthesis Inhibition Using Paclobutrazol", Functional Plant Biology, 2011, pp. 420-430, vol. 38.
Haiying et al., "Effects of different plant growth regulators on argronomic traits and yields of wheat", Journal of Seed Industry Guide, Nov. 10, 2014 pp. 12-13, No. 11.

(Continued)

*Primary Examiner* — Brent T Page
(74) *Attorney, Agent, or Firm* — MORRISON & FOERSTER LLP

(57) ABSTRACT

Provided are methods for increasing the yield of a monocot plant through treatment of the plant with a plant growth regulator. In certain embodiments, maize plants produce multiple ears and an increased number of kernels. In certain embodiments, reduced height of the plant allows for more efficient self-pollination.

22 Claims, 16 Drawing Sheets

(56) References Cited

OTHER PUBLICATIONS

Huang et al., "Physiology of wheat cultivation", Shanghai science and technology press, 1st Edition, pp. 71-76, Sep. 30, 1984.
Kasha et al., "High Frequency Haploid Production in Barley (Hordeum Vulgare L.)", Nature Publishing Group, Feb. 1970, pp. 874-876, vol. 225.
Li et al., "Morphology and anatomy of gramineae crops" Shanghai Sci. and Tech. Press, 1st Edition, p. 515, Jun. 30, 1979.
Li, et al., "Cultivation of dwarf seedling with polyprazole", Jiangxi Agri. Sci. and Tech., May 1, 1987, pp. 26-27.
Matthys-Rochon et al., "In Vitro Development of Maize Immature Embryos: A Tool for Embryogenesis Analysis", Journal of Experimental Botany, May 1998, pp. 839-845, vol. 49, No. 322.
Mei et al., "Basic principles of wheat production systems engineering", China environmental science press, 1st Edition, p. 68, Nov. 30, 1996.
Mulan et al., "Study on the effects of physiology, stigma activity and cross seed setting of uniconazole on ecological male sterile wheat", http://www.doc88.com/p-6177023255655.html, Aug. 27, 2014.
Prigge et al., "Production of Haploids and Doubled Haploids in Maize", Plant Cell Culture Protocols, Third Edition, pp. 161-172.
Rethwisch et al., "Comparision of Multiple Rate of Apogee and Palisade for 'Cheyenne' Bermudagrass Seed Production", Forage and Grain: A College of Agriculture and Life Sciences Report, College of Agriculture, Oct. 2004, pp. 59-62; Abstract, p. 60, para 2.
Rober et al., "In Vivo Haploid Induction in Maize—Performance of New Inducers and Significant of Doubled Haploid Lines in Hybrid Breeding", Maydica, 2005, pp. 275-283, vol. 50.
Rolston et al., "Grass Seed Yields Increase with Plant Growth Regulators and Fungicides" Proceeding of the New Zealand Grassland Association 66, 2004, pp. 127-132; Abstract, Table 1-2.
Schluttenhofer et al., "Use of Uniconazole to Control Plant Height for an Industrial/Pharmaceutical Maize Platform", Industrial Crops and Products, 2011, vol. 33, pp. 720-726.
Wang, et al., "Advanced plant physiology", China agricultural university press, 1st Edition, p. 330, Mar. 31, 2013.
Xu et al., "Co-Regulation of Ear Growth and Internode Elongation in Corn", Plant Growth Regulation, 2004, pp. 231-241, vol. 44.
Xu et al., "Paclobutrazol Improved the Reproductive Growth and the Quality of Seed Oil of Jatropha Curcas", Journal of Plant Growth Regulation, 2013, pp. 875-883, vol. 32.
Ye et al., "Modern pesticide application technology book", China Agriculture Press, 1st edition, pp. 456-457, Oct. 31, 2002.
Zhang, Qipeng, "Agricultural technology textbook—Crop cultivation", Dept. of Science and Education, Shanxi agriculture bureau, Shanxi scient and technology press, pp. 74-78, Feb. 28, 1984.
"A Brief Explanation of Terms of Agricultural Science and Technology", Information Research Institute of Shandong Academy of Agricultural Sciences, May 1, 1980, p. 5.
English Translation of First Office Action and Search Report for CN2016800433132, dated May 1, 2021.
English Translation of Second Office Action and Search Report for CN2016800460661, dated Dec. 1, 2020.
Yuju et al, "The New Pesticide is Safe and Useful", Zhongyuan Farmers Publishing House, June 30, 2011, pp. 337-338
Zhi'an, Zhang, "Experimental Techniques in Plant Physiology", Jilin University Press, Jul. 31, 2008, p. 173.
International Search Report and Written Opinion dated Oct. 19, 2016, for PCT Patent Application No. PCT/US2016/042608 filed on Jul. 15, 2016, seven pages.

* cited by examiner

MULTI-EAR SYSTEM TO ENHANCE MONOCOT PLANT YIELD

CROSS-REFERENCE TO RELATED APPLICATIONS

This application is a Continuation of U.S. National Phase Application Ser. No. 15/745,224, filed Jan. 16, 2018, which claims the benefit of is a 35 U.S.C. § 371 U.S. National Phase Application of International Patent Application No. PCT/US2016/042608, filed Jul. 15, 2016, which claims the benefit of U.S. Provisional Patent Application No. 62/193,389, filed on Jul. 16, 2015, all of which are incorporated herein by reference in their entireties.

BACKGROUND

The evolution and domestication of plants has generally followed a common pattern or "domestication syndrome" that distinguishes crops from their wild progenitors. One common domestication syndrome feature among crops arose from long-term selection for increased apical dominance, which is characterized by relatively more robust growth of a central stem and its buds and flowers in comparison to the growth of side stems and axillary buds, which has resulting in fewer and larger fruits per plant. The selection for apical dominance is considered an important symptom of domestication in many species, including the cereal crops of rice, wheat, barley and maize, as well as fruit crops like tomato.

A critical challenge during the domestication of crop plants was to improve the harvestability of the crop as compared to its progenitor. In unfavorable environments, wild plants often flower and mature rapidly; producing smaller numbers of branches, inflorescences, flowers and seeds in order to increase the likelihood of producing at least one offspring to continue the life cycle. In favorable environments, wild plants maximize the probability of successful reproduction by sequentially producing more branches, inflorescences, flowers and seeds over time. The latter strategy is not optimal for a crop as it is more efficient to harvest a fewer but larger fruit or inflorescences that mature synchronously from plant to plant which permits a single harvest at an optimal time of fruit or inflorescence maturation. Thus, diverse crops have been selected to produce smaller numbers of larger seeds, fruits or inflorescences on the main stem as a means of improving harvestability.

Perhaps the most striking and well-studied alteration in plant architecture was brought about by the domestication of maize. By selecting for traits that improve yield and mechanical harvestability, humans have transformed the progenitor of maize from a bushy, shrub-like ancestor with multiple elongated lateral branches tipped by male or female florescences into today's crop comprising a single, erect main stem with only two or three relatively abbreviated lateral branches, each terminating in a single female flower (ear). Today it is generally accepted that selecting for apical dominance in maize not only improves overall yield in ideal growing conditions, but it also makes the logistics of coordinating flowering times among and between lines much easier and streamlines field maintenance and mechanical harvestability.

The mechanism of apical dominance in maize involves the regulation of hormones such as auxin, which is produced by the apical meristem. As the primary ear begins to mature, greater amounts of auxin are produced by the apical meristem. The auxin is carried from the apical meristem down the plant and suppresses development of lower ears, resulting in secondary ears that are less likely to nick well or produce viable seed.

Methods for self-pollinated maize in controlled environment or nurseries have historically involved the removal of tillers and co-dominant ears because it is thought that these structures compete for resources or hormonally interfere with the primary ear and thus result in reduced grain yield. This approach likely dates back to the 1930's when corn tillers were called suckers because they were believed to 'suck' nutrients and sugar from the main plant. More recently research in field environments has shown that tillering is yield neutral for corn. However, farmers still prefer and select corn lines that do not tiller even in high growth environments. Both field and greenhouse plant densities are typically designed around production of plants with a single ear and tillering and ear prolificacy are often suppressed at these densities. A continuing need exists in the art for increasing seed or grain yield in monocot crop plants. In addition to broad acre yield, the ability to increase yield could be applied to breeding and increased seed production.

SUMMARY

Provided herein are methods for treating a monocot plant with a gibberellic acid-inhibitor (GA-inhibitor). Generally, the purpose is to increase seed yield of the monocot plant. In certain embodiments, the GA-inhibitor is administered to the plant by contacting the plant with the GA-inhibitor prior to the formation of a visible reproductive structure. In certain embodiments, the GA-inhibitor is administered by contacting the roots of the plant. In certain embodiments, the treatment reduces plant height.

In certain embodiments, the plant is an inbred V1 to V13 stage plant or a hybrid V1 to V15 stage plant. In certain embodiments, the GA-inhibitor is administered to the plant from the V1 stage up to about 10 days before the last tassel branch has emerged from the whorl (VT) [VT—10 days] and 2-3 days before silk emergence. In certain embodiments, the GA-inhibitor is administered from about 5 days post germination to about 40 days post germination. In certain embodiments, the plant is a wheat plant and the GA-inhibitor is administered prior to Feekes stage 6. In certain embodiments, the plant is treated at the V1, V2, V3, V4, or V5 stage and/or the plant is treated from about 5 days post germination to about 20 days post germination. In certain embodiments, the treatment induces tiller formation and/or increases tassel number. In certain embodiments, the plant is treated at the V6, V7, V8, or V9 stage and/or the plant is treated from about 21 days post germination to about 35 days post germination. In certain embodiments, the plant is a maize plant and the treatment induces co-dominant ears on the main stem. In certain embodiments, the plant is treated at the V10, V11, or V12 stage and/or the plant is treated from about 35 days post germination to about 40 days post germination. In certain embodiments, the plant is a maize plant and the treatment compresses the nodes above the primary ear. In certain embodiments, the plant is: i) first treated at the V1, V2, V3, V4, or V5 stage and/or treated from about 5 days post germination to about 20 days post germination and then ii) treated again at the V6, V7, V8, or V9 stage and/or treated again from about 21 days post germination to about 35 days post germination. In certain embodiments, the plant is iii) further treated at the V10, V11, or V12 stage and/or further treated from about 35 days post germination to about 40 days post germination. In certain embodiments, the plant is i) first treated at the V1, V2, V3, V4 or V5 stage and/or treated from about 5 days post germination to about 20 days post germination and then ii) treated again at the V10, V11, or V12 stage and/or treated again from about 35 days post germination to about 40 days post germination. In certain embodiments, the plant is i) first treated at the V6, V7, V8, or V9 stage and/or treated from about 21 days post germination to about 35 days post germination and then ii) treated again at the V10, V11, or V12 stage and/or treated again from about 35 days post germination to about 40 days post germination.

In certain embodiments, the GA-inhibitor is a triazole. Illustrative examples of triazole GA-inhibitors include, but are not limited to paclobutrazol, uniconazole, and flurprimidol. In certain embodiments, the GA-inhibitor is administered at a rate of at least 1.0 mg/plant. In certain embodiments, the GA-inhibitor is administered at a rate of from about 1.0 mg/plant to about 75 mg/plant, from about 1.0 mg/plant to about 50 mg/plant, or from about 1.0 to about 32 mg/plant. In certain embodiments, the plant is treated at the V1, V2, V3, V4, or V5 stage and/or the plant is treated from about 5 days post germination to about 20 days post germination and the GA-inhibitor is administered at a rate of from about 1.0 mg/plant to about 8.0 mg/plant or from about 1.5 mg/plant to about 5.0 mg/plant. In certain embodiments, the plant is treated at the V6, V7, V8, V9, V10, V11, or V12 stage and/or the plant is treated from about 21 days post germination to about 40 days post germination and the GA-inhibitor is administered at a rate of from about 8.0 mg/plant to about 50 mg/plant or from about 8.0 mg/plant to about 75 mg/plant.

In certain embodiments, the monocot plant is maize, wheat, rice, sorghum, or sugar cane. In certain embodiments, the monocot plant is maize or wheat.

In certain embodiments, the monocot plant is a maize plant and the treatment results in 1, 2, 3, 4, 5, 6, or 7 tillers on the treated plant. In certain embodiments, the tillers have delayed feminization and increased maleness. In certain embodiments, treatment with the GA-inhibitor increases pollen shed duration. In certain embodiments, the GA-inhibitor treated plant produces at least 1, 2, 3, 4, or 5, or more tillers than a control plant which was not contacted with the GA-inhibitor. In certain embodiments, the monocot plant is a wheat plant and the GA-inhibitor-treatment produces at least 4 or more tillers than a control plant which was not contacted with the GA-inhibitor. In certain embodiments, the method further comprises selecting a GA-inhibitor-treated plant that has tillers. In certain embodiments, wherein the treated plant is a maize plant, the method further comprises separating the tillers of the selected plant from the main stalk and replanting the tillers separately. In certain embodiments, one or more of the replanted tillers is treated with a GA-inhibitor. In certain embodiments, the replanted tillers produce more kernels in comparison to control tillers that are not separated from the main stalk.

In certain embodiments, the monocot plant is a maize plant and the GA-inhibitor-treatment results in: at least about 250 kernels from the treated plant; from about 250 kernels to about 600 kernels from the treated plant; at least about 600 kernels from the treated plant; from about 600 kernels to about 2000 kernels from the treated plant, from about 600 kernels to about 1000 kernels from the treated plant, or at least about 1000 kernels from the treated plant. In certain embodiments, the monocot plant is a wheat plant and the treatment results in the production of at least about 400 seeds from the treated plant. In certain embodiments, the monocot plant is a wheat plant and the treatment results in an increase in seed number of at least about 20% in comparison to an untreated control plant. In certain embodiments, the method further comprises harvesting the seed of a maize plant that produced at least about 250 kernels or harvesting the seed of a wheat plant that produced at least about 400 seeds. In certain embodiments, the method further comprises genotyping a harvested seed or a population of harvested seeds. In certain embodiments, the method further comprises using a harvested seed or a population of harvested seeds in a breeding program.

In certain embodiments, the treated plant is grown under controlled conditions. In certain embodiments, the treated plant is grown in a green house. In certain embodiments, the treated plant is grown in an open field. In certain embodiments, a population of commercially planted plants is treated and the treatment increases yield in comparison to a population of untreated control plants.

This disclosure also provides for methods of pollinating a maize plant, wherein the method comprises treating a maize plant according to any embodiment of GA-inhibitor treatment described herein and covering at least a portion of the maize plant, including the top of the plant and at least one ear, with a pollination bag. In certain embodiments, the plant covered by the pollination bag is a plant of reduced height. In certain embodiments, the pollination bag has a pore size of from about 75 to about 450 microns.

This disclosure also provides for methods of pollinating a maize plant, wherein the method comprises covering at least two plants with the same pollination bag, wherein at least one plant has been treated according to any embodiment of GA-inhibitor treatment described herein. In certain embodiments, at least one plant has its tassel or tassels removed and at least one plant has a tassel or tassels.

The disclosure also provides for a monocot plant produced by any embodiment of GA-inhibitor treatment described herein. The disclosure also provides for a monocot plant seed produced by any embodiment of GA-inhibitor treatment described herein and/or a monocot plant seed produced by any plant produced by any embodiment of GA-inhibitor treatment described herein.

DETAILED DESCRIPTION

Figure 1:
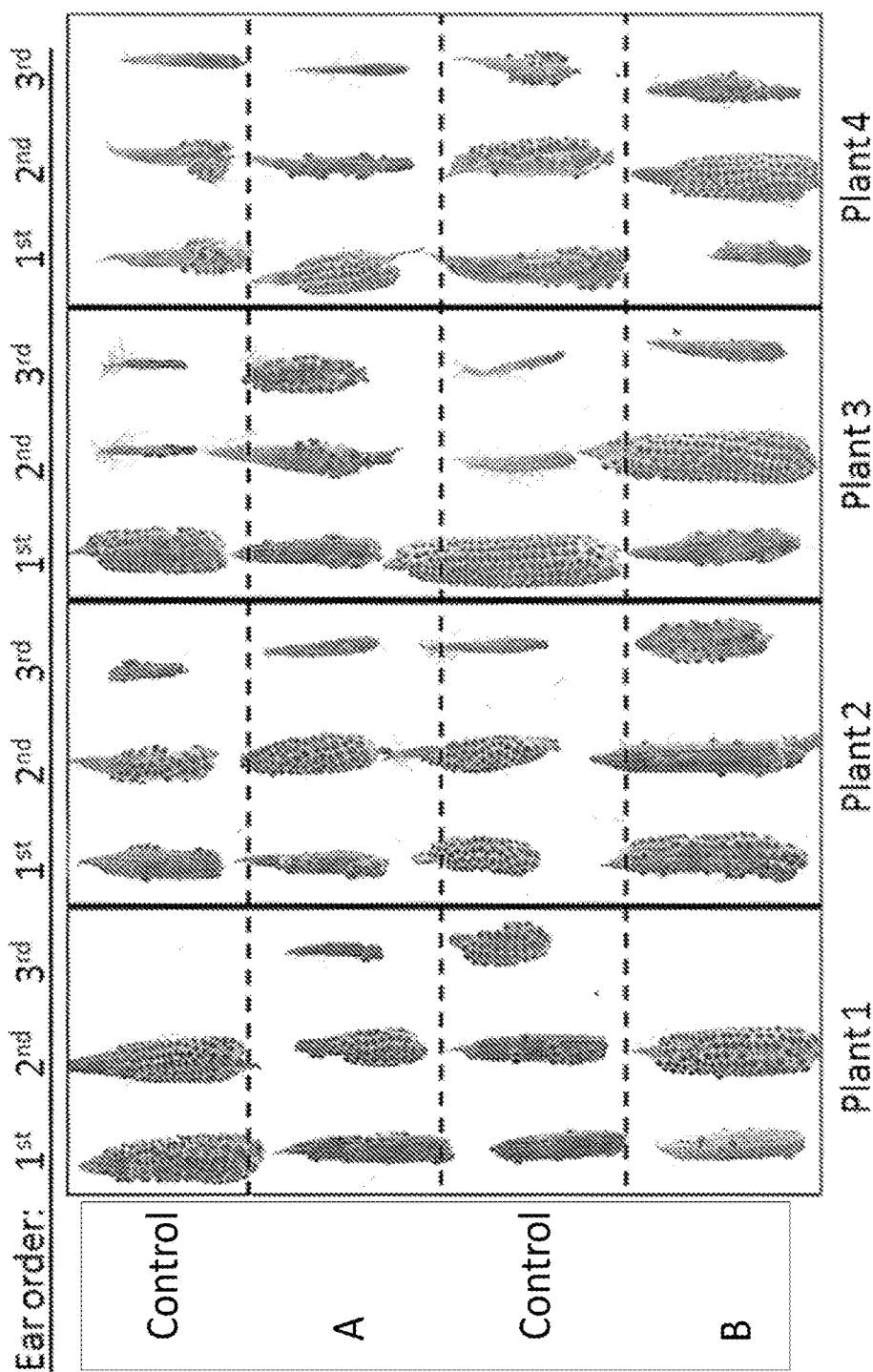
FIG. 1 shows ears classified by their population pedigree (A-D), position on the maize stalk, and number of $DH_1$ seed they produced.

Provided herein are methods of inducing or promoting the development of axillary meristems or additional side shoots or additional inflorescences in a crop plant. In certain aspects, this is done for the purpose of increasing yield, such as the number of seeds/grain produced by a monocot plant ("seed yield"). The methods provided can increase the yield of a single plant or when applied to a population of plants can increase the yield of the population of plants (such increasing the yield of a commercial harvest).

It is to be noted that the term "a" or "an" entity refers to one or more of that entity; for example, "a plant," is understood to represent one or more plants. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. Units, prefixes, and symbols are denoted in their Système International de Unites (SI) accepted form. Numeric ranges are inclusive of the numbers defining the range.

The headings provided herein are solely for ease of reference and are not limitations of the various aspects or aspects of the disclosure, which can be had by reference to the specification as a whole. Accordingly, the terms defined immediately below are more fully defined by reference to the specification in its entirety.

Definitions

A used herein, a "plant" refers to a whole monocot plant, any part thereof, or a cell or tissue culture derived from a monocot plant, comprising any of: whole plants, plant components or organs (e.g., leaves, stems, roots, etc), plant tissues, seeds, plant cells, and/or progeny of the same. A plant cell is a biological cell of a plant, taken from a monocot plant or derived through culture from a cell taken from a monocot plant.

As used herein, a "population of plants" or "plant population" refers to a plurality of plants. Commonly, the terms relate to a breeding population of plants from which members are selected and crossed to produce progeny in a breeding program. In such cases, a population of plants can be relatively small, e.g., such as can be housed in a greenhouse. The term can also refer to a plurality of plants planted, such as in an open field, for commercial or seed production purposes. In such cases, a population of plants can be very large, such as would be planted on hundreds or thousands of acres of land. In certain embodiments, a plurality may be 100 or more, 500 or more, or 1000 or more individual plants.

A population of plants can include the progeny of a single breeding cross or a plurality of breeding crosses. The population members need not be identical to the population members selected for use in subsequent cycles of analyses or those ultimately selected to obtain final progeny plants. Often, a plant population is derived from a single biparental cross, but may also derive from two or more crosses between the same or different parents.

As used herein, the term "genetic element" refers to either a recombinant DNA construct (commonly referred to as a "transgene") that has been inserted into the maize genome, a nucleotide sequence, or a genetic locus of a plant genome.

As use herein, the terms "promoting" and "inducing" are used interchangeably to mean either promoting, for example, promoting the development of axillary buds from preexisting buds or inducing, for example, inducing the formation of axillary buds de novo.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the terms "flower" and "inflorescence" are used interchangeably.

As used herein, the terms "maize" and "corn" are used interchangeably.

As used herein, the term "tiller," when referring to a maize plant tiller, is a branch from at or below the brace roots.

An "inbred" plant is a plant produced by self-pollination or backcrossing, generally repeated at least about seven times, to produce a pure-breeding strain. This means that if an inbred is self-pollinated, all of the progeny will be genetically identical or nearly identical to each other and to the inbred parent.

A "hybrid" plant is developed by crossing two different parent plants. A hybrid produced by crossing two inbreds developed from different but equally productive open-pollinated varieties usually will produce a more vigorous hybrid than one produced by crossing two inbreds from the same open-pollinated variety.

As used herein, the term "elite," "elite plant," and the like describes a group, germplasm, or population of at least one crop plant that has resulted from human-directed breeding and selection for superior agronomic performance. An "elite population" is an assortment of elite individuals or lines that can be used to represent the state of the art in terms of agronomically superior genotypes of a given crop species, such as maize. Similarly, an "elite germplasm" or "elite strain of germplasm" is an agronomically superior germplasm, typically derived from and/or capable of giving rise to a plant with superior agronomic performance, such as an existing or newly developed elite line of maize. In contrast, an "exotic plant," "exotic line," or "exotic germplasm" is a plant, line, or germplasm derived from a plant not belonging to an available elite line or strain of germplasm. In the context of a cross between two plants or lines of germplasm, an exotic germplasm is not closely related by descent to the elite germplasm with which it is crossed. Most commonly, the exotic germplasm is not derived from any known elite line of a crop, but rather is selected to introduce genetic elements (typically desired alleles) into a breeding program.

Seed production or seed manufacture refers to the amplification of seed, such as from a particular line or germplasm, so that enough seed is obtained for sale to customers and growers or other large scale planting.

Maize plants tend to produce a single dominate, or primary, ear that develops fastest and most completely. Additional ears sometimes form lower down the stalk from the dominant ear (the secondary ear is the next ear down from the primary ear, the tertiary ear next lowest, and so on—all of which can be referred to collectively as secondary ears), but their development is typically delayed with respect to the dominant ear. Because the development of additional, or non-dominant, ears is usually delayed, the dominant ear is typically the only one that nicks well.

As used herein, the term "co-dominant ear(s)" refers to ears on a maize plant that mature at a similar rate/time such that they produce silks receptive to pollen germination in an overlapping timeframe. A plant with co-dominant ears will have at least two co-dominant ears. Co-dominant ears can be numbered by their position on the stalk, i.e., the top co-dominant ear is the first co-dominant ear, the next co-dominant ear down from the first is the second co-dominant ear, the third co-dominant ear is the next lowest, and so on.

As used herein, a control plant (e.g., monocot control plant, maize control plant, etc.), is a plant (or population of plants) recognized as having a representative phenotype (e.g., number of inflorescences, number of tillers, number of ears, number of kernels/seeds, height, biomass, and the like), of a plant that has not been treated with a plant growth regulator but that is in other respects such as genetic makeup and growing conditions comparable to a plant treated with a plant growth regulator. For example, one of ordinary skill in the art would understand a control plant to have one or more of the following attributes: results from a seed derived from the same induction cross; has at least one parent in common with the treated plant; shares a common ancestor with the treated plant within twelve generations; shares sufficient common genetic heritage with the treated plant that one of ordinary skill in the art of plant breeding would recognize the control plant as a valid comparison for establishing a correlation between the application of a plant growth regulator and the resulting phenotype; and/or has one dominant ear and no co-dominant ears (maize). One of ordinary skill in the art will recognize that an untreated plant that by chance (e.g., a statistical outlier), by some other type of manipulation, or other reason comprises a phenotype that varies from a representative phenotype for the untreated plant would not be an appropriate control plant.

Chemistry Induced Yield Increase

Provided herein are methods of increasing the yield of a monocot plant by treating the monocot plant with a plant growth regulator (PGR). An increase in yield can be an increase in the number of seeds (seed yield) and/or an increase in other yield parameters including, but not limited to, grain weight and plant biomass. As used herein, an "increase," "increasing," or the like (or other comparative parameters such as reduced height) is in reference to a control plant or control population of plants as defined elsewhere herein.

In some embodiments, the increase in yield is an increase in seed yield of a monocot plant. Increasing the number of seeds produced by even one plant can be advantageous to plant breeders such as in reducing cycle time in breeding programs. Uniformity is generally a goal in breeding programs and thus in certain embodiments the treated plants are grown for at least a portion of the time under controlled conditions, such as in a greenhouse or other enclosed or partially enclosed structure. Conditions that may be controlled include irrigation, humidity, temperature, soil volume, light intensity, length of day/night, etc.

In certain embodiments, the treated plants are planted and grown, or transplanted and grown, exposed to the surrounding natural environment, such as in an open field. Commercial crops (broad acre farming) and seed production programs generally grow populations of plants comprising large numbers of plants in open fields. It is understood, however, that even in an open field, some parameters, for example irrigation, may be controlled to at least some extent. It is contemplated that treatment of a population of plants with a PGR according to present embodiments, such as in an open field, results in increased yield from the population of plants. Such increased yield could result in increased commercial output or increased seed amplification in manufacturing seed for seed production purposes.

It has been discovered that manipulation of certain traits, including increased yield, in a monocot plant can be achieved by control of one or more of specific chemistry, rate, timing, and application method. These traits include: reduced plant height; increased tiller number; increased tiller size and vigor; increased total plant biomass; increased axillary inflorescence (ear) number on tillers; increased axillary inflorescence (ear) number on the main stem; faster axillary inflorescence (ear) development on the main stem; increased maleness (more normal tassels) of tiller terminal inflorescences; increased pollen shed duration (believed to be from the presence of multiple tassels shedding over different time periods; increased single plant seed/kernel number and grain weight; increase visible root mass; increased stem diameter; improved overall plant health. It is believed that combinations of the above treatment-induced traits contribute to increased yield. In particular, as described elsewhere herein, one or more of increased tiller number, decreased height, and increased pollen shed duration can be particularly relevant to increasing yield.

In certain embodiments, a monocot plant is treated by administering to the plant a gibberellic acid-inhibitor (GA-inhibitor) to increase yield. In certain embodiments, the GA-inhibitor is a triazole. Representative examples of triazole GA-inhibitors include: Paclobutrazol-(±)-(R*, R*)-beta-((4-chlorophenyl)methyl)-alpha-(1,1,-dimethylethyl)-1H-1,2,4,-triazole-1-ethanol (Paclobutrazol or PBZ); Uniconazole-(E)-1-(4-chlorophenyl)-4,4-dimethyl-2-(1,2,4-triazol-1-yl)pent-1-en-3-ol (Uniconazole); Propiconazole-1-[[2-(2,4-dichlorophenyl)-4-propyl-1,3-dioxolan-2-yl] methyl]-1,2,4-triazole (Propiconazole); Flurprimidol-2-methyl-1-pyrimidin-5-yl-1-[4-(trifluoromethoxy)phenyl] propan-1-ol (Flurprimidol); Diniconazole-(E,3R)-1-(2,4-dichlorophenyl)-4,4-dimethyl-2-(1,2,4-triazol-1-yl)pent-1-en-3-ol (Diniconazole); and Metconazole-5-[(4-chlorophenyl)methyl]-2,2-dimethyl-1-(1,2,4-triazol-1-ylmethyl)cyclopentan-1-ol (Metconazole). In certain embodiments, the GA-inhibitor is paclobutrazol, uniconazole, or flurprimidol.

In certain embodiments, administration of the GA-inhibitor to the plant is by contact with the plant's roots. Contact of the GA-inhibitor with the roots of the plant can be achieved by any of various methods. For example, the exposed roots of a plant may be dipped into or otherwise contacted with a solution comprising the GA-inhibitor and then the plant is planted, a solution comprising the GA-inhibitor may be applied to the soil over and/or near the roots, or a container comprising the plant may be dipped into a solution comprising the GA-inhibitor so that the solution enters the container and contacts the roots such as by saturating the soil in the container. Alternatively, the GA-inhibitor may be a foliar or above-ground treatment applied to the leaves, stem, or other above-ground structures of the plant.

It has been observed that the chemistry (GA-inhibitor) generally takes up to 12-14 days to have an effect. Thus, the timing of the treatment is critical. In certain embodiments, the plant is treated with the GA-inhibitor prior to the formation of a visible reproductive structure. This timeframe is generally consistent with treating the plant at the V1 to V13 stage of development for an inbred plant or at the V1 to V15 stage of development for a hybrid plant and thus in certain embodiments, the plant is treated with the GA-inhibitor at the V1 to V13 stage for an inbred plant or at the V1 to V15 stage for a hybrid plant. This timeframe is also generally consistent with treating the plant from the V1 stage up to about 10 days before the last tassel branch has emerged from the whorl (VT) [VT—10 days] and 2-3 days before silk emergence. Thus in certain embodiments, the plant is treated with the GA-inhibitor from the V1 stage up to about 10 days before the last tassel branch has emerged from the whorl [VT—10 days] and 2-3 days before silk emergence. This timeframe is also generally consistent with treating the plant from about 5 days post germination to about 40 days post germination in the case of maize and thus in certain embodiments, the plant is treated from about 5 days post germination to about 40 days post germination. In certain embodiments where the plant is a wheat plant, the GA-inhibitor is administered prior to Feekes stage 6.

Further, this disclosure provides for treating a monocot plant with a GA-inhibitor to increase yield at one or more subsets of plant development stage/time occurring prior to the formation of a visible reproductive structure.

In certain embodiments, the plant is treated from about 5 days post germination to about 20 days post germination. This timeframe is generally consistent with the V1, V2, V3, V4, or V5 stage and thus in certain embodiments, the plant is treated at the V1, V2, V3, V4, or V5 stage. In certain embodiments, the plant is treated at the V4 or V5 stage. Treatment at these early times/stages has been associated with the inducement of tiller formation, resulting in an increased number of tillers. In maize, the formation of tillers or a greater number of tillers can lead in maize to an increased number of ears because the tillers are capable of forming ears in addition to ears on the main stem of the plant. In wheat, the formation of additional tillers can lead to an increased number of heads to produce seed. Treatment at these early times/stages has also been associated with increased maleness/tassel formation in maize. Both of these treatment induced attributes can lead to increased yield including increased seed number.

In certain embodiments, the plant is treated from about 21 days post germination to about 35 days post germination. This timeframe is generally consistent with the V6, V7, V8, or V9 stage and thus in certain embodiments, the plant is treated at the V6, V7, V8, or V9 stage. In certain embodiments, the plant is treated at the V7, V8, or V8 stage. Treatment at these later times/stages has been associated in maize with the inducement of increased ears, including co-dominant ears, on the main stem of the plant. Increased ear number can lead to increased yield including increased seed number.

In certain embodiments, the plant is treated from about 35 days post germination to about 40 days post germination. This timeframe is generally consistent with the V10, V11 or V12 stage and thus in certain embodiments, the plant is treated at the V10, V11, or V12 stage. In certain embodiments, the plant is treated at the V10 or V11 stage. Treatment at these latest times/stages has been associated in maize with compression of the nodes above the primary. This compression can bring one or more ears in closer proximity with the tassel(s) and thus increase the rate of pollination. Thus, compression of the nodes above the primary ear can lead to increased yield including increased seed number.

In certain embodiments, a plant can be treated at multiple times/stages to combine various treatment-induced attributes that can increase yield.

In certain embodiments, a plant is first treated at the V1, V2, V3, V4, or V5 stage and/or treated from about 5 days post germination to about 20 days post germination. The plant is then treated again at the V6, V7, V8, or V9 stage and/or treated again from about 21 days post germination to about 35 days post germination. In certain embodiments, the plant is further treated at the V10, V11, or V12 stage and/or further treated from about 35 days post germination to about 40 days post germination.

In certain embodiments, a plant is first treated at the V1, V2, V3, V4, or V5 stage and/or treated from about 5 days post germination to about 20 days post germination. The plant is then treated again at the V10, V11, or V12 stage and/or treated again from about 35 days post germination to about 40 days post germination.

In certain embodiments, a plant is first treated at the V6, V7, V8, or V9 stage and/or treated from about 21 days post germination to about 35 days post germination. The plant is then treated again at the V10, V11, or V12 stage and/or treated again from about 35 days post germination to about 40 days post germination.

GA-inhibitors can be administered to the plant in any number of forms. In certain embodiments, the GA-inhibitor is in a solution wherein only a percentage of the solution is the GA-inhibitor. Thus, the amount of solution or other medium applied can be determined to provide a certain amount or rate of GA-inhibitor to the plant. In certain embodiments, an effective amount of GA-inhibitor is applied to the plant. An effective amount is an amount that increases yield in at least one of the methods disclosed herein. In certain embodiments, the GA-inhibitor is administered at a rate of at least 1, 1.5, 2, 3, 4, 5, 6, 7, 8, 9, or 10 mg/plant. In certain embodiments, the GA-inhibitor is administered at a rate that does not exceed 32 mg/plant or does not exceed 50 mg/plant. In certain embodiments, the GA-inhibitor is administered at a rate of from about 1.0 mg/plant or about 1.5 mg/plant to any of about 5.0 mg/plant, 8.0 mg/plant, 10 mg/plant, 20 mg/plant, 32 mg/plant, 40 mg/plant, 50 mg/plant, or 75 mg/plant. In certain embodiments, the GA-inhibitor is administered at a rate of from about 8.0 mg/plant to any of about 10 mg/plant, 20 mg/plant, 32 mg/plant, 40 mg/plant, 50 mg/plant, or 75 mg/plant.

In certain embodiments, treatment at an early time/stage requires less GA-inhibitor to be effective. In certain embodiments, the plant is treated at the V1, V2, V3, V4, or V5 stage and/or the plant is treated from about 5 days post germination to about 20 days post germination and the GA-inhibitor is administered at a rate of from about 1.0 mg/plant or about 1.5 mg/plant to any of about 5.0 mg/plant, about 8.0 mg/plant, or about 10 mg/plant.

In certain embodiments, treatment at a later time/stage requires more GA-inhibitor to be effective. In certain embodiments, the plant is treated at the V6, V7, V8, V9, V10, V11, or V12 stage and/or the plant is treated from about 21 days post germination to about 40 days post germination and the GA-inhibitor is administered at a rate of from about 8.0 mg/plant, about 10 mg/plant, or about 15 mg/plant to any of about 20 mg/plant, 32 mg/plant, 40 mg/plant, 50 mg/plant, or 75 mg/plant.

In certain embodiments, increased yield, such as increased seed number, can be attributed at least in part to tiller induction. In certain embodiments, treatment with a GA-inhibitor induces tiller formation. In certain embodiments, treatment with a GA-inhibitor increases the number of tillers on a treated plant compared to an untreated control. In certain embodiments, treatment results in a treated plant with at least 1, 2, 3, 4, or 5 more tillers than an untreated control. In certain embodiments, wherein the plant is a maize plant, treatment results in a maize plant with 1, 2, 3, 4, 5, 6, or 7 tillers. In certain embodiments, wherein the plant is a wheat plant, treatment results in a wheat plant with at least 14 tillers.

Because of the discovered potential for yield increase, in certain embodiments, a GA-inhibitor treated plant with tillers is selected. The selected plant may be grown with the tillers attached to the main stalk. In certain embodiments, however, the tillers are separated from the main stalk. These separated tillers can be replanted. These replanted tillers can be grown such as to produce seed. It has been discovered with maize that when removed and separately grown, the number of maize kernels from the main stalk and separately grown tillers combined can be greater than the number of combined kernels produced by a plants main stalk and tillers where the tillers remained attached. It has also been discovered that when removed and separately grown, the number of maize kernels from the separately grown tillers combined can be greater than the number of combined kernels produced by the tillers where the tillers remained attached to the main stalk. In certain embodiments, a replanted tiller can be treated with GA-inhibitor, such as to further increase the yield from that tiller compared to an untreated tiller.

Increase in seed number is beneficial in plant development and breeding programs to increase screening capacity and/or produce enough seed to provide statistically significant research results. In certain embodiments, the seed of a GA-inhibitor treated plant is harvested. In certain embodiments, the harvested seed is screened in some manner, for example to determine a genotype or phenotype. In certain embodiments, the harvested seed is genotyped. In certain embodiments, the harvested seed is planted. In certain embodiments, the plant grown from the harvested seed is grown without GA-inhibitor treatment. Because GA-inhibitor treatment does not change the genotype of the plant, the offspring of a GA-inhibitor-treated plant will not exhibit the attributes of increased tiller production, reduced height, increased seed number, etc. of a treated plant. In certain embodiments, the plant grown from the harvested seed is also treated with a GA-inhibitor as described herein.

In certain embodiments, increased yield can be attributed at least in part to an increase in the number of ears on a treated maize plant. This increase in the number of ears can be from the induction of tillers that produce ears, the induction of multiple ears on the main stalk (such as co-dominant ears), or both. While tiller formation is generally not desired, for example in maize planted in a field where spacing is carefully controlled, it is contemplated that the treatment of a population of plants according to a method of this disclosure may also be used to increase commercial broad acre yield or to increase the production of seed in the manufacture of seed through tiller induction and/or multiple main stalk ear induction. Thus in certain embodiments, a population of plants in the field, such as commercially planted plants or plants for seed production, is treated with a GA-inhibitor as described herein to increase yield of the treated population in comparison to an untreated control population.

In certain embodiments, increased yield can be attributed at least in part to a reduction in plant height of treated plants. For example, generally maize is a tall plant. The physical distance between the ear and the tassel on a maize plant can itself pose a hurdle for pollination. By reducing the height of the plant, this distance is decreased, and thus can increase the rate of self-pollination. Further, the size of a normal maize plant makes covering the plant challenging. By reducing the height of the plant, some or all of the plant can be easily covered for the purposes of increasing self-pollination. In certain embodiments, at least a portion of a plant is covered with a pollination bag. In certain embodiments, the bag encompasses from the top of the plant and covering the lowest ear node. In certain embodiments, the bag covers the top of the plant and at least one ear. In certain embodiments, the bag covers the entire plant above the ground.

In certain embodiments, the bag can have one or more of the following attributes: it is a blend of high density and low density polyethylene thermoplastic sheeting (e.g., vispore (X-6606 product number) from Tredegar Plastics); its thickness by weight=1.75 mm; its embossed thickness=23 mils; its holes size in millimeters=18; its holes size in microns=75 to 450; the fabric is clear and allows air and light to pass through.

In certain embodiments, a plant is treated with a GA-inhibitor as described herein to reduce the height of the plant. A self-pollination bag is placed over at least a portion of the plant or over the entire plant (whole plant bagging method) just before pollen shed. The bag is removed when pollen shed is done in the zone including any neighboring plants. Vigorous air movement and shaking of plants and bags can increase seed set.

A self-pollinating bag can also be placed over at least a portion of two or more plants grown in proximity in the same or different containers or in the field (referred to as "auto-hybridization"), such as a male inbred corn plant and a female inbred corn plant. In certain embodiments, the plants are covered just before pollen shed. This method can allow, for example, hybridization between the two inbred corn germplasm lines on a more continual basis within the time of pollen shed. Advantages of this self-bag/auto-self hybridization method include increased efficiency from reducing the need for time and labor. In certain embodiments, the method comprises covering at least two plants with the same pollination bag, wherein at least one plant has been treated according to a method of GA-inhibitor-treatment of at least one of the present embodiments. Because treatment with a GA-inhibitor can result in a plant with reduced height, in certain embodiments, all the plants covered by the bag are treated in order to make them a generally consistent height for the pollination bag to fit over. In certain embodiments, at least one plant has its tassel or tassels removed and at least one plant has a tassel or tassels in order to generate pollen. In certain embodiments, two plants are covered with the same pollination bag and one plant has its tassel or tassels removed and one plant has a tassel or tassels. In certain embodiments, the tassel or tassels are removed from the female plant in the cross.

Figure 12:
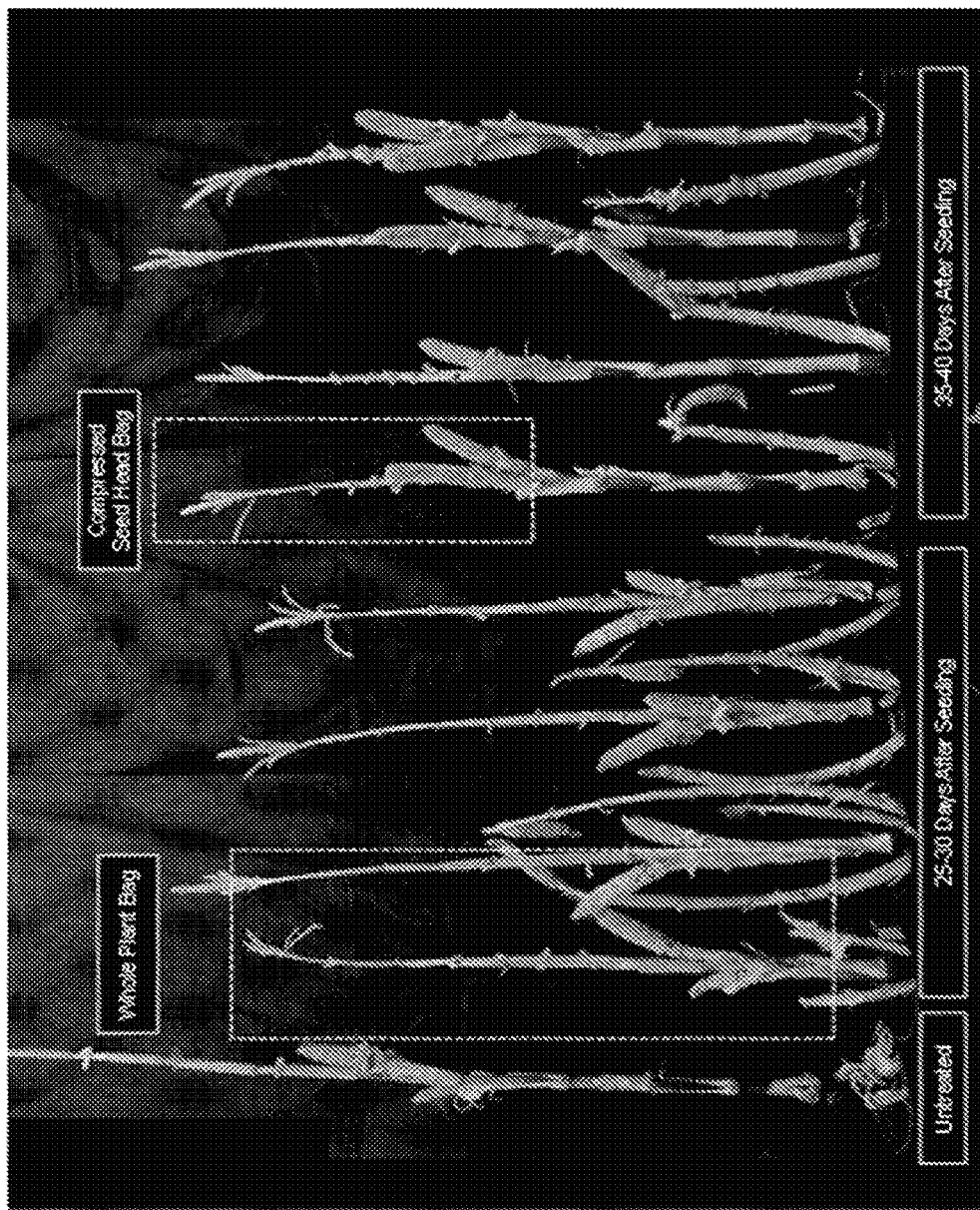
FIG. 12 shows a comparison between early and late GA-inhibitor treatment and the results on node compression.

In certain embodiments, treatment with the GA-inhibitor is at 35-40 days after seeding (or comparable developmental stage), resulting in compressed nodes above the primary ears. This brings the tassel in close proximity to the silks. Late treatment allows for only bagging the upper portion of the plant rather than earlier treatment which does not compress the upper nodes and thus lends itself to whole plant bagging. This correlation between early and later treatment and the proximity of the tassel to the silks is shown in FIG. 12.

In certain embodiments, a treated plant has a minimum amount of seeds that is generally greater than the number of seeds obtained from non-treated plants. For example in maize, field nursery yields can be around 100 kernels per plants (kpp) and treatment with a GA-inhibitor according to present embodiments can increase this yield. In certain embodiments, GA-inhibitor-treatment results in at least about 250 kpp, at least about 600 kpp, or at least about 1000 kpp. In certain embodiments, GA-inhibitor-treatments results in from about 250 kpp to any of about 600 kpp, about 1000 kpp, or about 2000 kpp. In certain embodiments, GA-inhibitor-treatments results in from about 600 kpp to any of about 1000 kpp or about 2000 kpp. In certain embodiments, GA-inhibitor-treatments results in from about 1000 kpp to about 2000 kpp.

The methods provided also increase yield in wheat. In certain embodiments, GA-inhibitor-treatment of a wheat plant results in production of at least about 400 seeds from the treated plant. In certain embodiments, GA-inhibitor treatment of a wheat plant results in an increase in seed number of at least about 20% in comparison to an untreated control plant.

Earlier treatments with a GA-inhibitor in general result in larger increases in yield and/or seed numbers. In maize, this may be in part because earlier treatment can induce tiller formation and thus the potential for a greater number of ears. Earlier treatments may also be combined with later treatments. Later treatments only, however, can still result in increased yield and may provide advantages such as to plant morphology that are desirable such as to control pollination.

In certain embodiments, the seeds from a GA-inhibitor-treated plant with a certain number of seed is harvested, such as for use in a breeding program or in a seed production operation. In certain embodiments, seed of a maize plant that produced at least about 200 kernels, at least about 600 kernels, at least about 1000 kernels, or at least about 2000 kernels is collected, harvested, etc. In certain embodiments, seed of a wheat plant that produced at least about 400 seeds is collected, harvested, etc. This seed can be screened for genotypic or phenotypic traits, such as by genotyping, for use for example, in a breeding program. This seed can also be used for commercial planting or for use in the amplification of additional seed such as in a seed production program.

Certain embodiments provide for a monocot plant produced by any of the present methods disclosed herein including plants having increased yield, increased seed yield, increased number of tillers, increased number of ears, and/or a specified number of tillers, ears, and/or kernels/seeds, etc. Certain embodiments provide for a population of monocot plant produced by any of the present methods disclosed herein including a population having increased yield, increased seed yield, increased number of tillers, increased number of ears, and/or a specified number of tillers, ears, and/or kernels/seeds, etc.

Certain embodiments provide for a monocot plant seed produced by any of the present methods disclosed herein including seeds from plants having increased yield, increased seed yield, increased number of tillers, increased number of ears, and/or a specified number of tillers, ears, and/or kernels/seeds, etc.

Doubling Efficiencies

Haploid sporophyte plants contain a gametic chromosome number (n) and can originate spontaneously or through artificial induction. Haploids tend to be less vigorous and less fertile than a sporophyte of similar genotype with the zygotic chromosome number (2n), and so are of limited direct benefit to researchers seeking to improve plant genetics.

Although spontaneous chromosome doubling does occur, the frequency is so low (typically less than 5%), that researchers attempting to create doubled haploids plants ("DH plants") often subject haploid plants to treatments that promote chromosome doubling. Haploid plant seedlings subjected to a chromosome doubling treatment can produce haploid egg and/or sperm, and if these plants are successfully selfed, the zygotic chromosome number can be recovered in the offspring, thus restoring the vigor and fertility expected of a 2n sporophyte.

During chromosome doubling, each homologue is replicated to create a substantially identical copy of the original and thus the entire genome of a DH plant is usually considered homozygous at each locus. This process can create completely homozygous and homogenous lines in fewer generations than traditional backcrossing, thereby improving selection efficacy, reducing the number and length of breeding cycles, and consuming fewer resources.

The likelihood of generating large numbers of doubled haploid offspring from a given haploid plant using methods currently known in the art is so low, however, that it severely reduces the advantages of incorporating them on a large scale in a competitive breeding program. As far back as the 1950s researchers have been attempting to improve doubling rates in plants and have developed techniques for over 250 crop species. However, even the best methods described reliably yield doubling rates of only 12% or less and typically depend on the application of the anti-microtubule drug colchicine, which is toxic to plants at the concentrations required. The effects are also highly genotype specific.

Furthermore, current doubling methods are labor intensive and often require that plants are handled several times during treatment, reducing their survival rate. Haploid plants often become so fragile during colchicine treatment that even if they live through it and are successfully doubled, they do not survive the subsequent handling and downstream processing steps necessary to transplant them to a field, greenhouse, or other growth conditions where they can recover and eventually grow to produce seed. Thus, plant breeders and researchers will typically use a gauge that characterizes both the likelihood that a haploid plant is doubled as well as the likelihood that the plant survives to produce doubled haploid seed when comparing the overall effectiveness of one doubling method to another.

Haploid plants subjected to a chromosome doubling treatment (or in certain embodiments haploid plants to be subjected to a chromosome doubling treatment) termed $DH_0$ plants, by contact with the chromosome doubling agent can produce haploid egg and/or sperm, and if the $DH_0$ plants are successfully selfed, the zygotic chromosome number can be recovered in the offspring (termed $DH_1$ seeds, plants, etc.), thus restoring the vigor and fertility expected of a 2n sporophyte. "Doubling Efficiency" (DE) is an overall gauge of doubling success calculated by dividing the number of $DH_0$ plants of a designation that produce $DH_1$ seed by the total number of $DH_0$ plants of that designation that were subjected to a chromosome doubling treatment.

While recovery of a single $DH_1$ seed can technically be counted as a successful doubling event, plant breeders usually require a population of at least several plants in order to generate the statistical power necessary to draw confident conclusions from their genetic and statistical tests. For example, a doubling treatment that produces only one or a few $DH_1$ seeds will be of limited use in a competitive breeding program because at least one additional generation of planting, growing, pollinating, and harvesting will be required to generate a sufficient population size for accurate statistical testing, especially if comparisons across multiple environments are planned. In a relatively large breeding program this seed "bulking" step will push testing of that population back an entire season, which typically delays release of a commercial product by at least one year.

In order to better quantify doubling treatment efficacy, minimum yield constraints can be applied during the process of calculating DE such that a given $DH_0$ plant must produce at least a minimum number of $DH_1$ seeds before it is counted in the proportion of successful doubling events, i.e. used in the numerator. Subscripts can be used to signify the minimum yield constraint such that $DE_{20}$ is the doubling efficiency calculated when only $DH_0$ plants that produced at least 20 $DH_1$ seeds are divided by the total number of $DH_0$ plants subjected to the doubling treatment. $DE_{30}$ represents the DE when only the $DH_0$ plants that produced at least 30 $DH_1$ seeds are divided by the total number of $DH_0$ plants subjected to the doubling treatment. Similarly, $DE_{50}$ represents the DE when only the $DH_0$ plants that produced at least 50 $DH_1$ seeds are divided by the total number of $DH_0$ plants subjected to the doubling treatment and so on.

Axillary Bud Induction and Promotion

Described herein is the discovery that it is now possible to dramatically increase the likelihood of recovering a target number of seeds in a single generation from a $DH_0$ monocot plant. Methods comprise inducing or promoting the monocot plant to develop at least one of a variety of different types of axillary buds that can give rise to additional inflorescences. Different embodiments of axillary bud induction and/or treating plants at different growth stages to control the type of axillary bud(s) that develop are possible. Non-limiting examples include multibuds, tillers, and co-dominant ears, which are defined in detail herein.

Axillary bud induction in monocots relaxes the apical dominance that normally inhibits the development of side shoots and/or secondary flowers or inflorescences. In certain embodiments a user causes a mother plant to produce a greater number of fertile female inflorescence and fertile female eggs than current methods of plant breeding and crop cultivation which focus on maximizing the development of a single female inflorescence.

Although known to sometimes arise and develop spontaneously, the formation or development of axillary buds in maize is presently an undesirable trait that is eliminated from breeding programs for a number of reasons described herein. Among these is the idea that hormones responsible for maintaining apical dominance will suppress the development of axillary bud flowers, so it is more efficient if the plant does not waste resources developing them or the vegetative structures that support them. This is especially apparent in modern maize hybrids, where yields are typically maximized in good environments by growing hybrids selected to focus their resources on developing a single, super-performing ear that nicks well and minimize the development of any axillary buds or secondary inflorescences.

It has been discovered, however, that by subjecting a monocot plant to at least one of several possible axillary bud induction treatments at one or more of many possible points in the plant's life cycle it is possible to release the developmental programming for greater apical dominance that plant breeders have selected for. In certain embodiments, a user subjects a monocot plant to a treatment that promotes the development of at least one pre-existing or primordial axillary bud such that it either forms a lateral side shoot (e.g. a tiller) or a secondary (or tertiary, or quaternary, etc.) inflorescence on the main stem of a maize plant. A user can sync the development of at least one axillary bud on a maize plant with the development of other buds on the maize plant to effect a simultaneous and coordinated development of at least two ears on the plant that exhibit the traits expected of a dominant ear, including being receptive to pollination at about the same time (e.g. co-dominant ears). Descriptions and examples herein enable a user to chooses and/or develop an appropriate combination of induction treatment parameters from a wide range of options to suit specific needs. Certain embodiments include subjecting a plant to a treatment that resets the developmental program of at least one cell in the nodal region of the main stem such that it gives rise to at least one new lateral shoot meristem that develops into a new lateral branch capable of producing fertile inflorescences (e.g. multibuds).

Thus, in certain embodiments, a user can confidently recover a target number of seed from a $DH_0$ monocot plant by inducing it to form additional flowers from axillary buds, pollinating those flowers, and then harvesting the seed that form from those additional flowers until the target number of seeds is obtained. By combining all the seeds produced by a plant induced to form additional axillary buds one can increase the chances of producing a desired number of seeds from a single mother plant in a single generation.

Nick

In maize, successful kernel formation requires an overlap in timeframe when the female structures necessary to support fertilization are fully functional and the timeframe when pollen is viable and released from the tassel. Good nick describes circumstances when the overlap in those timeframes is sufficient to fertilize most, if not all, of the available ovaries on the ear. Because pollen can be sensitive to desiccation, heat, and other environmental factors, the timeframe for good nick is often limited to several days or even a few hours. If pollen is released too soon such that most or all of it is non-viable by the time the female flowers are receptive to pollination, then nick will be poor, leading to many unfertilized eggs and poor seed set. Nick is also expected to be poor when pollen is released so late that the silks are dead or the female flowers are otherwise no longer receptive and/or capable of supporting fertilization. Under normal growth conditions the development of secondary ears is usually suppressed and delayed so that the primary ear is typically the only whose development is sufficiently aligned with that of the tassel for good nick to occur.

Nick serves such a crucial connection in the maize life cycle that commercial producers and maize breeders alike spend considerable resources helping ensure it. It is not uncommon for a competitive or industrial breeding program to cull lines otherwise exhibiting excellent performance but do not nick well and thus their maintenance becomes uneconomical. For example, a population of $DH_0$ plants may exhibit a very high rate of doubling and contain excellent genetics, but may still be eliminated from further development if it nicks so poorly that it is a struggle to produce sufficient seed to self and/or maintain or if more than one generation is required to produce sufficient seed for performance testing.

Plant Treatment Agents

In certain embodiments provided herein, a plant can be contacted with a wide variety of "plant treatment agents." Thus, as used herein, a "plant treatment agent", or "treatment agent", or "agent" can refer to any exogenously-provided compound that can be introduced to the surface of a plant and migrate into a plant tissue. In some embodiments, the plant treatment agent acts extracellularly within the plant tissue, such as interacting with receptors on the outer cell surface. In some embodiments, the plant treatment agent enters into cells within the tissue. In some embodiments, the plant treatment agent is contained within a liquid. Such liquids include, but are not limited to, solutions, suspensions, emulsions, and colloidal dispersions.

Contacting a plant with a treatment agent can occur before, during, or after the application of other substances. In certain embodiments, contact between the plant and the treatment agent is achieved by dipping, submerging, or otherwise inserting the plant into a reservoir of liquid comprising the plant treatment agent. Other methods of contacting a plant with a treatment agent include spraying or misting the plant with a solution comprising a plant treatment agent or agitating or tumbling a plant in a solution comprising a plant treatment agent. In certain embodiments, contact between the plant and the treatment agent is achieved by a soil drench, which comprises adding a liquid treatment agent to the soil or growth medium near the roots where the plant will grow.

In certain embodiments, liquids are of an aqueous nature. In certain embodiments, aqueous liquids can comprise water soluble components. In certain embodiments, aqueous liquids can comprise water insoluble components, can comprise an insoluble component that is made soluble in water by addition of a surfactant, or can comprise any combination of soluble components, insoluble components, and surfactants.

A "plant treatment solution" or "treatment solution" can refer to any solution of liquid that comprises a plant treatment agent. In certain embodiments, a plant treatment solution comprises a plant treatment agent and the two terms can often be used synonymously. For example, delivering a plant treatment solution comprising the plant treatment agent colchicine to a plant meristem is essentially synonymous with delivering a plant treatment agent comprising colchicine to a plant meristem.

Plant treatment agents include, but are not limited to, macromolecules including polynucleotides including nucleic acids (e.g. DNA and/or RNA), polypeptides, polysaccharides, polyketides, and the like. Polynucleotides can be single-stranded or double-stranded and can include antisense molecules and interfering RNAs. Polynucleotides can include mutations and/or various other modifications, such as to their backbones, that are well known in the art. Polynucleotides include "genetic elements", which comprise recombinant DNA constructs (commonly referred to as "transgenes") that have been inserted into a plant genome, or a nucleotide sequence, or a genetic locus of a plant genome. Thus, in certain embodiments, a user of this invention can deliver a sequence of DNA or RNA to a targeted tissue to alter the expression or inheritance of a plant trait, for example, to effectively "transform" a plant by inserting a genetic element into its genome.

Plant treatment agents can also comprise various phytohormones, phytohormone agonists, phytohormone antagonists, or agents that stimulate or inhibit phytohormone perception, signaling or synthesis. In certain embodiments, a plant treatment agent comprises a plant growth regulator (PGR). PGRs are a class of compounds that affect the cellular processes, growth, development or behavior of a plant or plant part. In some embodiments a PGR is responsible for accelerating or retarding the rate of growth or maturation or otherwise altering the behavior of a plant or plant part. In some embodiments, a PGR is a naturally-occurring plant hormone. In some embodiments, a PGR is an chemical alters flowering, internode length, apical dominance, ripening, root architecture, or fruiting, including any substance that affects growth, development, behavior, or reproduction in a monocot plant. Plant growth regulators include auxins (e.g. IAA) and auxin inhibitors, cytokinins (e.g. BAP) and cytokinin inhibitors, compounds that can stimulate ethylene production (i.e. ACC and the like) and compounds that can inhibit ethylene production (AVG and the like), and compounds that inhibit ethylene perception (silver and the like). Plant growth regulators also comprise compounds that modulate plant perception, signaling, and/or behavior, such as giberrellins and their inhibitors (also referred to herein as gibberellic acid-inhibitors (GA-inhibitors)), abscisic acid and its inhibitors, and jasmonic acid and its inhibitors. Other examples include peptide hormones, for example, systemin, phytosulfokine, rapid alkalinization factor and the like.

IAA is indole-3-acetic acid, and IBA is inodole-3-butyric acid. Both are naturally-occurring forms of a class of plant hormones called auxins. Other variations of auxin can be used, including synthetic auxins, such as 2,4-D (2,4-Dichlorophenoxyactic acid and α-NAA (α-Naphthalene acetic acid).

BAP is 6-Benzylaminopurine, N-(Phenylmethyl)-7H-pruin-6-amine, also written as C12H11N5. IAA is indole-3-acetic acid, and IBA is inodole-3-butyric acid. Both are naturally-occurring forms of a class of plant hormones called auxins. Other variations of auxin can be used with this invention, including synthetic auxins, such as 2,4-D (2,4-Dichlorophenoxyactic acid) and 1-NAA (1-Naphthalene acetic acid).

In general, plant treatment agents used herein will be water soluble agents. However, the use of plant treatment agents with high, intermediate, low or negligible water solubility can, in certain embodiments, be facilitated by the use of liquid compositions that also comprise various transfer or conditioning agents. Transfer or conditioning agents can comprise any agent that facilitates migration of plant treatment agents to the plant (e.g., plant cells) and/or that facilitate uptake of plant treatment agents by the plant. Transfer or conditioning agents include, but are not limited to, (a) surfactants, (b) an organic solvents or an aqueous solutions or aqueous mixtures of organic solvents, (c) oxidizing agents, (d) acids, (e) bases, (f) oils, (g) enzymes, or combinations thereof. In certain embodiments, methods can optionally include an incubation step, a neutralization step (e.g., to neutralize an acid, base, or oxidizing agent, or to inactivate an enzyme), a rinsing step, or combinations thereof whereby the liquid and plant treatment agent contained therein is treated either before or after delivery to the plant. Transfer or conditioning agents thus include, but are not limited to, emulsions, reverse emulsions, liposomes, and other micellar-like compositions. Examples of useful adjuvants include surfactants and effective molecules contained therein, which include sodium or lithium salts of fatty acids (such as tallow or tallowamines or phospholipids). Transfer or conditioning agents can comprise salts including, but not limited to, sodium, ammonium, calcium, lithium, magnesium, chloride, sulfide, and sulfate salts. Certain embodiments of the methods provided herein use counter-ions or other molecules that are known to associate with plant treatment agents. For certain negatively charged plant treatment agents such as polynucleotides, cations such as inorganic ammonium ions, alkyl ammonium ions, lithium ions, polyamines such as spermine, spermidine, or putrescine, and the like can be used. Organic solvents useful in conditioning a plant cell to permeation with certain plant treatment agents including, but not limited to polynucleotides, are solvents such as DMSO, DMF, pyridine, N-pyrrolidine, hexamethyiphosphoramide, acetonitrile, dioxane, polypropylene glycol, or other solvents that are miscible with water. Naturally derived or synthetic oils with or without surfactants or emulsifiers can be used, e.g., plant-sourced oils, crop oils (such as those listed in the 9th Compendium of Herbicide Adjuvants, publicly available on the world wide web (internet) at "herbicide.adjuvants.com") can be used. Oils useful in certain liquid compositions used in the methods provided herein include, but are not limited to, paraffinic oils, polyol fatty acid esters, or oils with short-chain molecules modified with amides or polyamines such as polyethyleneimine or N-pyrrolidine.

In certain embodiments, a plant treatment agent can be a chromosomal doubling agent. Chromosome doubling agents are used to generate doubled haploid plant cells and doubled haploid plants. Chromosomal doubling agents can comprise various mitotic inhibitors that cause chromosome doubling. In certain embodiments, the chromosome doubling agent can be a compound such as colchicine, amiprophos methyl, trifluralin, oryzalin, pronamide, or chloropropham. In still other embodiments, the chromosome doubling agent can be a low mammalian toxicity chromosomal doubling agent. Various low mammalian toxicity chromosome doubling agents that can be used include, but are not limited to, compounds such as: i) 1,2,3-trimethoxy-4-((1S,6R)-6-nitro-cyclohex-3-enyl)-benzene and other related compounds disclosed in US Patent Application Publication 2010/0169999; and ii) compounds disclosed in U.S. Pat. No. 5,866,513 to Michelotti et al. U.S. Patent Application Publication 2010/0169999 and U.S. Pat. No. 5,866,513 are incorporated herein by reference in their entireties. In particular, the 76 compounds disclosed in Table I and 1a on Cols. 3-4, 5-6, and 7-8 of U.S. Pat. No. 5,866,513 are each incorporated herein by reference. In certain embodiments, the chromosome doubling agent is a polynucleotide.

In certain embodiments, a broad range of chemical concentrations and dosing schedules can be used in conjunction with these methods and one of ordinary skill in the art can optimize the dose administered to a given genotype in order to maximize co-dominant ear formation and/or maximize nicking and/or fertilization among co-dominant ears.

Types of Plants

Unless otherwise specified, this disclosure is not limited to any particular type of monocot plant. For example, in certain embodiments, the monocot plant is a member of the family Poaceae, wheat plant, maize plant, sweet corn plant, rice plant, wild rice plant, barley plant, rye, millet plant, sorghum plant, sugar cane plant, turfgrass plant, bamboo plant, oat plant, brome-grass plant, Miscanthus plant, pampas grass plant, switchgrass (Panicum) plant, and/or teosinte plant, or is a member of the family Alliaceae, onion plant, leek plant, garlic plant.

Unless otherwise specified, as used herein, a plant may be any whole monocot plant, or part of a monocot plant, or tissue culture derived from a monocot plant, or monocot plant seed; having a tissue to which a plant treatment agent can be delivered. A plant may be of various chromosomal content, such as haploid, diploid, triploid, tetraploid, etc. Polyploidy refers generally to a condition of having a ploidy level greater than triploid. In certain embodiments, a distinction is made between plant tissues grown in tissue culture and non-tissue culture plants.

Unless otherwise specified, as used herein, the surface of a plant refers to the surface that is generally exposed to the external environment surrounding the plant without pulling, cutting, etc. the plant to expose additional areas. For example, if a plant is submerged completely in a solution, the surface of the plant is generally the portion of the plant that would come in contact with the solution.

A plant tissue can be any plant tissue. In certain embodiments, a plant tissue can include a functional meristem or grouping of cells capable of forming a functional meristem. A functional meristem is defined as a center of pluripotent cells that has the ability to give rise to new plant tissues or organs. In certain embodiments, the plant tissue comprises a meristem tissue such as a root apical meristem or a shoot apical meristem.

In certain embodiments, a plant treatment agent is delivered to a targeted or selected plant tissue. A plant tissue can be targeted or selected based on the tissue's response to the plant treatment agent and/or the influence over the plants growth, characteristics, genetics, yield, etc., that is sought to be achieved. For example, the shoot apical meristem, particularly of a $DH_0$ plant, can be selected for the delivery of a chromosome doubling agent. The selected tissue can be located at the surface of the plant and/or it can be located beneath the plant surface or beneath a portion of the plant surface. Thus, in certain embodiments, wherein even the entire surface of a plant is contacted by a solution comprising a plant treatment agent such as by completely submerging the plant, at least a portion of the selected tissue may not be contacted by the solution.

In certain embodiments, prior to germination, the plant or a propagule of the plant is contacted with a plant treatment agent in order to deliver the treatment agent to at least one selected tissue of the plant. In certain embodiments, embryo rescue techniques known in the art are used to excise an embryo from the seed prior to germination of the seed in order to better contact the embryo to the treatment agent. After excision, the embryo can be cultured in vitro or otherwise grown in conditions that promote its survival and development into a seedling. Thus, delivery of a plant treatment agent to selected tissues of a plant prior to germination can be improved using a variety of techniques currently known in the art, including embryo rescue techniques, thereby allowing the embryo to be contacted by the plant treatment agent. In certain embodiments, these methods are used to deliver a doubling agent to a meristem of a haploid embryo in order to create at least one doubled haploid reproductive tissue capable of producing functional, haploid gametes.

A monocot plant for use in methods described herein can be at any of various developmental stages. For example, maize plants can be described by their vegetative growth and reproductive stages, and as used herein, the stages of maize kernel development (Leaf Collar method: V1-Vn, Vt, R1-R6, etc.) are as described in Abendroth, L. J., R. W. Elmore, M. J. Boyer, and S. K. Marlay, 2011, Corn Growth and Development, PMR 1009, Iowa State University Extension, Ames, Iowa. For example, wheat plants can be described according to the following chart of seedling development (Table A):

TABLE A

| Haun | Feekes | Zadoks | General Desription |
|---|---|---|---|
| 1 | | 10 | First leaf emerged |
| 1.+ | | 11 | First leaf unfolded |
| 1.+ | | 12 | 2 leaves unfolded |
| 2.+ | | 13 | 3 leaves unfolded |
| 3.+ | | 14 | 4 leaves unfolded |
| 4.+ | | 15 | 5 leaves unfolded |
| 5.+ | | 16 | 6 leaves unfolded |
| 6.+ | | 17 | 7 leaves unfolded |
| 7.+ | | 18 | 8 leaves unfolded |
| 8.+ | | 19 | 9 or more leaves unfolded |

In certain embodiments, the monocot plant is a maize plant. In certain embodiments, the monocot plant is a maize plant and the plant tissue is a meristem. In certain embodiments, the monocot plant is a maize plant and the plant tissue comprises a shoot apical meristem (SAM). In certain embodiments, the monocot plant is a maize plant, the plant tissue comprises a shoot apical meristem, and the maize plant is within the seed or germinating or at or between the VE, V1, V2, V3, V4, V5, V6, V7, V8, V9, V10, V11, or V12 vegetative growth stage. In certain embodiments, the monocot plant is a haploid maize plant, the plant tissue comprises a shoot apical meristem, the maize plant is within the seed or germinating or at or between the VE, V1, V2, V3, V4, V5, V6, V7, V8, V9, V10, V11, or V12 vegetative growth stage.

Methods described herein are not restricted by certain stages of a plant's development. It is anticipated that techniques of prolonging or otherwise modifying the duration of growth stages could be used in conjunction with this invention to expand a user's options of when to apply a PGR in order to induce development of additional shoot apical meristems and/or axillary buds and/or codominant ears.

Methods for Producing Doubled Haploid Plants

Certain embodiments described herein provide solutions to a problem that those of ordinary skill in the art have been struggling to solve for decades. This problem is how to ensure that substantially any doubled $DH_0$ plant will produce a desired number of $DH_1$ seeds in a single generation. In certain embodiments, the likelihood of recovering at least a minimum number of $DH_1$ seeds from a $DH_0$ plant (for example, at least one $DH_1$ seed, at least four $DH_1$ seeds, at least twenty $DH_1$ seeds, etc.) can be improved by inducing or promoting a $DH_0$ plant to develop at least one additional axillary bud. This process can be repeated with other axial buds, simultaneously and/or sequentially, until a target number of seeds is generated. By combining the seeds produced by at least one axillary bud with the seeds produced by at least one other axillary bud, and/or the seed produced by the primary bud of a $DH_0$ mother plant, these methods can improve the likelihood of recovering dozens, hundreds, or even thousands of $DH_1$ seeds from a single $DH_0$ plant.

Colchicine-based chromosome doubling protocols generally suggest exposures of several minutes to several hours and rely on the hope that during that time not only does the colchicine specifically contact cells of the shoot apical meristem that will give rise to reproductive organs, but also that the contact occurs during the specific periods of the cell cycle necessary for chromosome doubling to occur. The uncertainties of this translate into the problems of low maize doubling predictability and efficiency problems that plant breeders have been struggling to solve for many years.

In certain embodiments, the unpredictability of current DH methods can be decreased by increasing the number of chances each single mother $DH_0$ maize plant has of meeting the conditions necessary to produce a doubled-haploid inflorescence. It has been discovered that a single haploid maize plant can now be induced to produce a target number of $DH_1$ offspring with much greater frequency and reliability. Haploid plants can be induced to form multiple axillary meristems into fertile fruit-bearing structures to produce greater numbers of $DH_1$ seed as compared to control plants that have not been induced in such a manner.

Haploid monocot plants that are used for obtaining doubled haploid plants, seeds, and/or cells can be acquired by any method. In certain embodiments, haploid maize plants, or the haploid ears derived from them, can be obtained by crossing an inducer line (male) with a desired line (as female) to induce haploid plant cell formation in the female line. Exemplary inducer lines for maize include, but are not limited to, Stock 6, RWS, KEMS, Krasnodar Haploid Inducer (KHI), KMS or ZMS, lines comprising an indeterminate gametophyte (ig) mutation, and derivatives thereof. In other embodiments, wide hybridization crosses can be used to produce haploids. Exemplary descriptions of wide hybridization crosses can be found in Kasha and Kao, 1970, Nature 225:874-876. Any other method of haploid induction could also be used with these methods, including molecular or transgenic-based approaches, for example, those involving CENH3 alterations or other genome degradation-based methods.

Certain embodiments provide for methods of obtaining a doubled haploid maize plant cell, the method comprising contacting a maize plant with a solution that comprises a plant treatment agent, wherein the plant treatment agent is a chromosome doubling agent, and allowing the doubling agent to cause formation of at least one doubled-haploid plant cell. Also provided herein are methods of obtaining a doubled haploid maize plant cell, the method comprising harvesting a doubled haploid plant cell from a seed comprising a doubled-haploid plant cell. In certain embodiments, the seed is on the ear of maize as the plant cell is harvested from the seed.

Certain embodiments provide methods of obtaining a doubled-haploid maize plant, the method comprising obtaining a doubled-haploid maize embryo derived by any of the methods provided herein and supplying sufficient nutrients to the embryo to permit development of the embryo into the doubled-haploid maize plant seed. A doubled-haploid maize embryo can be formed by methods comprising performing any of the aforementioned methods of delivering a solution comprising a plant treatment agent into the shoot apical meristem, wherein the plant treatment agent is a chromosome doubling agent, and allowing the doubling agent to induce chromosome doubling.

In certain embodiments of these methods, the doubled-haploid maize plant cell is obtained from a third party. In other words, the party who caused the formation of the doubled-haploid maize plant cell is not necessarily the party who supplies the nutrients to permit development of the plant cell into the doubled-haploid maize plant.

Also provided herein are methods of obtaining a seed comprising a doubled-haploid maize plant cell, the method comprising harvesting a seed comprising a doubled-haploid plant cell obtained by the methods of obtaining a doubled-haploid maize plant cell. A doubled-haploid maize plant cell can be obtained by methods comprising performing any of the aforementioned methods of delivering a solution comprising an plant treatment agent into the plant wherein the plant treatment agent is a chromosome doubling agent, and allowing the doubling agent to induce formation of at least one doubled-haploid plant cell in at least one of the seeds. In certain embodiments, the harvested seed is a physiologically mature seed.

Also provided herein are methods of obtaining a doubled-haploid maize plant, the method comprising sowing a seed comprising a doubled-haploid maize plant cell obtained by the methods of obtaining a seed comprising a doubled-haploid maize plant cell, and permitting the sown seed to develop into the doubled-haploid maize plant. In certain embodiments, the seed comprising the doubled-haploid maize plant cell is obtained from a third party. In other words, the party who harvested the seed is not necessarily the party who sowed the seed comprising the doubled-haploid plant cell and permitted the sown seed to develop into the doubled-haploid maize plant.

In certain embodiments, doubled haploid plant cells can be obtained by harvesting $DH_1$ seed from a DH maize ear that forms on a $DH_0$ plant treated with a chromosome doubling agent by the methods provided herein. Physiologically mature $DH_1$ seed derived from the DH ear on the $DH_0$ mother plant can be harvested to obtain a doubled haploid plant cell that is contained in the seed. Physiologically mature $DH_1$ seed from the treated DH ear the $DH_0$ plant can also be sown and permitted to germinate to obtain a doubled haploid maize plant.

In certain embodiments, a haploid plant cell can be recovered from a maize ear treated with a chromosome doubling agent by rescuing a plant cell from a kernel on the ear. Plant cell rescue can be performed by removing a treated plant cell from an ear, placing the plant cell in media that provides for plant cell and/or plant development, and allowing plant cell and/or plant development to occur. In certain embodiments, media that provides for plant cell and/or plant development can include one or more phytohormones, salts, and/or sugars. Various media and techniques for plant cell rescue are described in Matthys-Rochon, et al., Journal of Experimental Botany, Vol. 49, No. 322, pp. 839-845, 1998.

These methods can be adjusted for a wide range of parameters in order to maximize nicking among the co-dominant ears of substantially any genotype of plants. One of ordinary skill in the art can adjust these methods for any number of variables known to affect plant development in conjunction with these methods, including altering planting density, dosage, chemical treatment methods or timing to improve nick and/or fertilization and/or seed production in a diverse range of plant genotypes or germplasms. In certain embodiments, plants can be planted at different densities to affect co-dominant ear formation. In certain embodiments, plants can be treated with at least one of many possible chemical agents (e.g. agents that affect ear formation like GA-inhibitors), using at least one of many possible dosage levels to optimize formation and nicking among at least two co-dominant ears in substantially any genotype or set of genotypes. In some embodiments, some other treatment known in the art to affect plant development can be provided in order to optimize co-dominant ear formation. In some embodiments, a combination of the above can be used to optimize co-dominant ear formation. In some embodiments, different treatments can be used on different genotypes in order to optimize overall co-dominant ear formation.

Plant Breeding

Methods provided herein can be used to increase the efficiency of plant breeding in monocots by increasing the number of recombinant offspring that a given mother plant produces in a single generation. This realization has dramatic and broad applications to plant breeding as it increases the likelihood that a single monocot plant will produce offspring containing a statistically unlikely yet superior combination of genetic elements. A plant breeder employing these methods to integrate certain DNA sequences, genotypes, and/or phenotypic traits into a target germplasm and/or genome will be able to create a gamete containing a sequence of DNA comprising a specific set of genetic elements using fewer mother plants and using fewer resources than a breeder using current methods known in the art. This is due, in part, to the fact that the methods described herein effectively enable a user to induce mother plants to produce more seeds per plant, which equates to more meioses per plant, which equates to more opportunities per plant for a desired genetic recombination to occur. More recombination opportunities per plant therefore translates to fewer plants (and fewer resources) needed to reach an effective population size necessary to achieve a high likelihood of recovering at least one plant with a desired combination of genetic elements.

For example, when plant breeders use recurrent selection to introgress a desired genetic element into a target germplasm, they rely on genetic recombination to occur between the homologous chromosomes of the target germplasm and the donor germplasm in loci the genomes flanking the desired genetic locus. A user of these methods will have a greater likelihood of generating a mother plant with a genome comprising the target germplasm modified only by the sequence(s) of the donor genome necessary to confer the desired genetic element because these methods generate more recombination events per mother plant, and thus a user will have a greater likelihood of creating a plant containing the desired arrangement of genetic elements incorporated into its genome than a user of other trait integration methods.

The benefits of this become even more apparent when trying to introgress multiple genetic elements into a target germplasm because the number of genetic recombination events required to introgress additional genetic elements into a target germplasm rapidly increases with the number of additional genetic elements desired to be introgressed. A user of these methods will find they need far fewer mother plants to achieve a high likelihood of recovering the desired introgression event(s), and thus, can dramatically increase the efficiency of creating a desired arrangement of genetic elements in a gamete as compared to one using current methods in the art that ignore axillary buds and/or do not deliberately induce axillary buds to produce fruit.

This realization is especially useful in inflorescent monocot species, for example maize, because each time an additional inflorescence is induced to form, an entire ear worth of potential ovules (on average 500 kernels or more for most high-yielding hybrids), each representing an opportunity for the required genetic recombinations to occur during meiosis. Thus, a breeder of ordinary skill in the art can use these methods to dramatically increase the efficiency of creating a desired arrangement of genetic elements in a gamete as compared to one using current methods in the art that ignore axillary buds or do not deliberately induce them to form and produce fruit.

These methods can be combined with any method of prolonging nick, prolonging pollen shed, or prolonging the period during which ears are receptive to pollination and fertilization that are known in the art. For example, a tassel can be subjected to a treatment that prolongs the period during which the tassel sheds pollen. T pollen that is shed can be preserved in order to extend the period of time that it is capable of successful pollination and subsequent fertilization. Other methods known to improve or extend nick can also be employed.

In certain embodiments, axillary bud induction treatments can be applied at the VE, V1, V2, V3, V4, V5, V6, V7, V8, V9, V10, V11, or V12 growth stages, or any combination thereof.

Multibuds

One type of induced axillary bud is a "multibud", which is derived by inducing a plant to form a de novo axillary bud from differentiated cells. This method effectively reprograms one or more cells of a plant to produce a de novo meristem, shoot or axillary bud.

In certain embodiments, a monocot seedling or a monocot plant embryo can be subjected to axillary bud induction while still attached to the seed (direct seed approach) or the seedling/embryo can be dissected from the seed before germination (dissected embryo method), or the seedling/embryo can be separated from the seed after germination (embryo axis method).

Disclosed herein is the discovery of several novel uses for multibuds in monocots, including the improvement of doubling efficiency ("DH"), by ensuring that a target number of seeds is generated from a cross or self. In certain embodiments, a user desiring to ensure that at least a minimum number of seeds is generated in a single generation by a $DH_0$ plant induces the $DH_0$ plant to form at least one doubled-haploid multibud. In certain embodiments, at least one of these multibuds is grown into a mature haploid plant that is selfed to produce $DH_1$ seed. This process can be repeated, simultaneously and/or sequentially, until the desired target number of seeds is generated.

In certain embodiments, these methods can first increase the number of doubled-haploid seed recovered by inducing a diploid parent plant to produce at least two diploid multibuds which are then grown into mature diploid plants. These multibud-derived parent plants can then be pollinated with an inducer to form at least one haploid seed, which can be subsequently grow into seedlings and subjected to chromosome doubling techniques known in the art to convert the haploids into a population of $DH_0$ plants. The $DH_0$ plants can then be grown until they produce flowers, and then pollinated to produce $DH_1$ seeds.

In certain embodiments, a single diploid plant can be subjected to a multibud induction treatment to generate several diploid multibuds. These multibuds can be separated from the mother plant and grown until they produce flowers, at which time they can be pollinated by an inducer. Even if some multibud-derived ears produce very few or no seeds, it is expected that this method can be repeated, either sequentially or simultaneously, until a target number of seeds are generated when all seeds from multibud-derived ears are combined. As many of these haploid plants as are necessary can be subjected to chromosome doubling to produce a desired number of DH plants.

The haploid seeds recovered and pooled from at least one multibud-induced ear can be subjected to any manner of analyses the user deems appropriate in order to determine which seeds contain specific traits. These analyses can include sorting the seeds (including the embryos and all other tissues of the seed) to identify and separate out diploid seeds, including the haploid sorting methods described in U.S. patent application Ser. No. 14/206,238 which published as US20140266196A1 and which is incorporated by reference herein in its entirety. Analyses can also include genotyping tissues using methods known in the art. Regardless of how the haploid seeds are analyzed, a subset of the population can be selected based on any criterion in order to limit the number of plants that are subjected to subsequent doubling steps. Thus, these methods can reduce the amount of resources spent doubling plants that do not meet a target selection threshold.

Unlike current methods of producing DH plants, a user of these methods does not rely on only a single chance at doubling the cells necessary to produce an ear containing at least the target number of haploid eggs. Rather, the user is able to produce multiple ears from a single $DH_0$ plant, and thus combines multiple doubling opportunities to achieve a target number of haploid eggs.

Tillers

Tillers are a type of axillary bud. The induction of tillers in monocots relaxes the suppression inhibiting the development of an axillary bud so that the axillary bud is able to form an elongated side shoot that ultimately produces a tassel and at least one female flower known as an ear. Although known to form spontaneously, the formation of tillers is an undesirable trait that is eliminated from maize breeding programs for a number of reasons, including the fact that they make preserving the identity of neighboring plants more difficult and increase the likelihood of cross-contaminating seeds of different experimental treatments. They also tend to overgrow the area normally allotted to an individual plant, which upsets planting arrangements, makes human and machine access more difficult, and disrupts efficient field maintenance, cultivation, and harvest. Furthermore, tillers compete with the mother plant (i.e. the main stem from which the tillers were derived) for nearby resources, reducing the accuracy of phenotype evaluations and overall yield per unit acre. For these and other reasons, tillers are generally eliminated from research plots and commercial operations alike.

It has been discovered, however, that by subjecting a maize plant to an axillary bud induction treatment at specific times in the plant life cycle it is possible to generate multiple tiller shoots from a single mother plant that produce ears which nick well with the tassels of the same shoot and produce excellent seed set when pollinated. Thus, these methods can increase the chance of recovering a target number of seed produced by a single maize plant by inducing it to form tillers, allowing those tillers to produce their own ears, and then harvesting the seeds from at least one of the ears produced by at least one of the tillers. By combining the seeds produced by at least one tiller with the seeds produced by at least one other tiller, and/or the seed produced by the mother plant, these methods can increase the chance of recovering dozens, hundreds, or even thousands of seeds from a single plant.

In certain embodiments, a method comprises inducing a $DH_0$ plant to form at least one doubled haploid tiller. At least one of these tillers is grown into a mature haploid plant that is selfed to produce $DH_1$ seed. The process can be repeated, simultaneously and/or sequentially, until a target number of seeds is generated. By combining the seeds produced by at least one tiller with the seeds produced by at least one other tiller, and/or the seed produced by the $DH_0$ mother plant, these methods can increase the chance of recovering of dozens, hundreds, or even thousands of seeds from a single $DH_0$ plant.

Unlike current methods of producing DH plants, these methods are not limited a single chance at doubling the cells necessary to produce an ear or tassel containing at least the target number of haploid eggs or pollen. Rather, they produce multiple ears and tassels from a single $DH_0$ plant, thus combining multiple doubling opportunities to produce an ear containing at least the target number of haploid eggs and pollen, and subsequent to pollination and fertilization, the target number of $DH_1$ seed.

Co-Dominant Ears

Certain embodiments provide for the production of co-dominant ears. In certain embodiments, the development of co-dominant ears is coordinated such that at least two co-dominant ears are receptive to pollination at a time that overlaps with pollen shed from tassels of the same plant. In certain embodiments, the development of co-dominant ears is coordinated such that at least two co-dominant ears are receptive to pollination at a time that overlaps with pollen shed from tassels of another desired germplasm.

Certain embodiments comprise subjecting a plant to an axillary bud induction treatment at specific times in a plant's life cycle. It is possible to generate at least two co-dominant ears on a single plant whose development is coordinated such that the ears nick well and produce excellent seed set when pollinated. These methods can increase the recovery of a target number of offspring seed from a single parent plant by inducing the parent plant to form multiple co-dominant ears that are all receptive to pollination in overlapping timeframes.

In certain embodiments, seeds are generated in a single generation by a $DH_0$ plant by inducing the $DH_0$ plant to form at least two co-dominant ears after doubling treatment. Unlike conventional methods of producing DH plants, these methods do not rely on only a single chance at doubling the cells necessary to produce an ear containing at least the target number of haploid eggs. Rather, multiple ears are produced from a single $DH_0$ plant, thus combining multiple doubling opportunities to produce the at least target number of haploid gametes, and subsequent to pollination and fertilization, for example to produce the target number of $DH_1$ seed.

An unexpected observation has a considerable impact on DH production. Once a $DH_0$ plant is treated with induction agent, it is not entirely predictable as to which ear on the $DH_0$ plant will produce the greatest number of $DH_1$ seed. In some cases, the second and/or third ear had better seed set than the first ear. Surprisingly, in some cases the first ear yielded few seeds or no seeds whatsoever while the second and/or third ears yielded abundant seeds.

Furthermore, representative results described herein reveal that it is stochastic as to which ear has the most doubling potential. It was demonstrated that it is not predictable which axillary meristems along the shoot are most likely to be doubled by a chromosome doubling treatment even among the closely-related members of an inbred line.

In cases where so many co-dominant ears have formed on the mother plant that there are insufficient resources to fully support their development, the ears may be cultured separately, e.g. in vitro, in separate pots, or in any other way known in the art.

In certain embodiments, the co-dominant ear induction treatment comprises applying a plant treatment agent to a plant. In certain embodiments, the plant treatment agent is a plant hormone or combination of plant hormones. In certain embodiments, the co-dominant ear induction treatment comprises applying a gibberellic acid-inhibitor (GA-inhibitor), such as PBZ, uniconazole, chlormequat-CL, mepiquat-CL, AMO-1618, clorphonium-Cl, tetcylacis, ancymidol, flurprimidol, paclobutrazol, uniconazole-P, inabenfide, prohexadione-CA, trinexapac-ethyl, daminozide, exo-16,17-, or dihydro-$GA_5$-13-acetate or a combination of any plant treatment agents, for example, a GA inhibitor combination with cytokinin.

In certain embodiments, the co-dominant ears are formed on different shoots. For example, a user can treat a main stem (i.e. the mother plant) with a plant treatment agent to cause the main stem to form at least one tiller. The user times the treatment in order to coordinate the development of an ear on the tiller (i.e. a tiller ear) and an ear on the mother plant such that both ears produce silks and are receptive to pollination in a substantially-overlapping timeframe. In certain embodiments, the user treats a mother plant to form at least two tillers and times the treatments in order to coordinate the development of at least two tiller ears growing from different tillers so that the at least two tiller ears produce silks receptive to pollination during a substantially-overlapping timeframe. Thus, methods involving tillers and methods involving co-dominant ears are not mutually exclusive; it is possible to incorporate both types of axillary bud formation methods to achieve enhanced results in certain situations.

EXAMPLES

The following examples are included to demonstrate certain embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

In the following examples, haploid maize seeds were obtained by pollinating F1 or F2 females containing desired genetics with pollen from a haploid inducer line. Ears were harvested when the seeds were mature, the ears were then shelled, and then the seeds sorted into haploid vs. diploids. Haploid maize plants used herein were obtained by pollinating F1 or F2 maize plants with pollen from a haploid inducer line to form F1 hybrid-derived haploid induction populations. Ears were harvested when the seeds were mature, shelled, and the haploid seeds recovered by standard methods of the art.

Non-limiting examples of haploid inducer lines that can be used to repeat the experiments below include Stock 6 (Coe 1959), RWS (Rober et al. 1005), KEMS (Deimling et al. 1997), KMS or ZMS (Chalyk et al. 3994; Chalyk and Chebotar 1000), or other inducer lines derived from these. The inducer line may also carry at least one marker trait to facilitate the identification of haploid offspring. The purity of the haploid pool can be made to be 95% or greater and can be verified using a variety of methods known in the art.

Example 1. Maize Ear Prolificacy can be Manipulated to Produce Multiple Ears Per Plant Across Diverse Germplasms V1-V3 seedlings of two unique F1 hybrid-derived haploid maize lines, derived from: female heterotic group (Germplasm A) or male heterotic group (Germplasm B), were subjected to a bulk colchicine-based chromosome doubling treatment by removing the seedlings from soil or growth media at the V1-V3 growth stage and aligning their stems and wrapping them together along with several wooden rods into bundle a held together by a strip of aluminum foil (approximate foil strip dimensions were 6 in×18 in). The bundled plants were submerged in plant treatment solution comprising 1250 ppm of colchicine in a centrifuge container and then the entire sample was centrifuged at 50 g for 3 min while the shoot apical meristems (SAMs) remained submerged in the plant treatment agent solution.

Following the first centrifugation, the plant treatment solution was decanted and the seedlings subjected to an addition centrifugation at 335 g for 3 min. During the second centrifugation, the rod-wrap bundle supported the seedlings and prevented the SAMs from contacting the reserve treatment agent that was not absorbed by the plant during application of the centrifugal force.

Following the second centrifugation, the plants were removed from the centrifugation container and the rod-wrap bundle and rinsed with water to remove any remaining colchicine solution, and then recovered and tended in a light, humidity, and temperature-controlled greenhouse for several days before being transplanted to a nursery greenhouse. These centrifuge-based treatment methods are described in more detail in International application number PCT/US2015/028955, which is incorporated by reference herein in its entirety, however, standard doubling treatments can also be applied to any of the haploid doubling steps referred to herein.

Following colchicine doubling treatment, 15-20 plants from each germplasm were planted in pots at two different densities; either as single plants per pot (singles), or as two plants per pot (pairs).

Next, each plant received one of two different doses of PBZ, either 50 mL (low dose) or 60 mL (high dose) of a 2.5% PBZ solution (v/v; 0.4% of active ingredient) in water. These two different doses were applied by soil drench at either the V7 or V8 growth stage, which occurred a total of 23 or 26 days after the seedlings had been subjected to chromosome doubling treatment, respectively. A control group of plants received no treatment solution but were otherwise treated exactly as the experimental groups planted as singles. When pollen shed began at the tassels, the average number of silk-producing ears (i.e. co-dominant ears) were counted for each dosage, germplasm, and treatment time and the results summarized in Table. 1.

TABLE 1

The number of co-dominant ears formed per plant in two unique induced haploid germplasms (A and B) following treatments at one of two different doses of PBZ at one of two different developmental stages following chromosome doubling treatment.

| | | Planted as Singles | | Planted as Pairs | |
|---|---|---|---|---|---|
| Growth Stage† | Germplasm | Low Dose | High Dose | Low Dose | High Dose |
| V7 | B | 2.7 | 3.3 | 1.5 | 1.5 |
| | A | 3.4 | 3.9 | 3 | 3.4 |
| V8 | B | 2.3 | 2.2 | 1.5 | 1.5 |
| | A | 2.3 | 3.5 | 2.3 | 2.2 |

†V7 occurred 23 days after chromosome doubling treatment; V8 occurred 26 days after chromosome doubling treatment.

The control plants for Germplasm A and B produced 1.4 EP and 1.1 EP, respectively.

These results reveal that these methods remain useful among different planting densities. Both germplasms formed more co-dominant ears when individuals were planted singly in pots, regardless of treatment timing. All paired Germplasm B plants produced fewer ears than any of the singled Germplasm B plants, regardless of dosage or treatment timing, and the high-dose V8 Germplasm B population produced more than twice their doubled counterparts. This variance in the effect that planting density has on different germplasms provides a user with the understanding that the optimum range of planting densities that one can employ in conjunction with these methods can vary from germplasm to germplasm. It is expected that a user can adjust treatment timing and other growth or treatment conditions to optimize use of these methods with different germplasms.

These results reveal that across the variables of dosage, density, and germplasm, treatments applied at both V7 and V8 consistently produce more co-dominant ears for both germplasms than the controls. Thus, these methods are not limited to the application of co-dominant ear induction treatment during a particular point of plant development. In one embodiment, co-dominant ear induction treatment occurs at a range of times selected by the user which improve the number of seeds produced by a haploid plant treated with a chromosome doubling agent.

The results reveal that these methods are not limited to use with specific germplasms or plant genotypes. Furthermore, both germplasms showed varying improvements depending on other variables, such as planting density, treatment schedules, dosages and other variables. The number of co-dominant ears was improved for two drastically divergent genotypes over a range of different treatment schedules. It is anticipated that users will use these methods with a wide range of other germplasms and will be able to adjust parameters such as planting density, the timing of ear induction treatment(s), the dosage of chemicals used during ear induction treatment(s), and other variables that affect ear development to maximize nick among co-dominant ears and improve the number of seed produced in a given generation.

These results reveal that the use of these methods is not limited to specific dosages of chemicals that induce ear formation. A variety of different ear per plant (EP) improvements appear to correlate with dosage. For one, the average EP of all plants treated with the high dosage was 0.31 greater than the EP of all plants treated with the low dosage. This relationship is even more pronounced when only the singles were considered (the high-dose EP average was 0.55 higher than the low-dose). Furthermore, singles subjected to the low dose still produced a minimum increase of 1.2 EP over control plants, suggesting there are dosage effects even outside of the range tested here that could be used in conjunction with these methods.

Example 2. Harvesting and Pooling the Seeds of co-Dominant Ears Improves the Recovery of $DH_1$ Seeds in a Single Generation An F1 hybrid-derived haploid induction population derived from female inbred maize plant Germplasm A was germinated in soil and tended in standard greenhouse maize growing conditions for approximately seven days. Seedlings were then subjected to a bulk colchicine-based chromosome doubling treatment as described above. Following treatment, seedlings were transplanted into pots and tended in a greenhouse at standard greenhouse maize growing conditions to recover.

Twenty-nine days after the colchicine doubling treatment, 77 of the $DH_0$ seedlings were subjected to a co-dominant ear induction treatment comprising the addition of 60 mL of 2.5% PBZ (v/v) in water, which was poured into the soil surrounding the roots of each plant. The seedlings were then tended in standard greenhouse maize growing conditions until they flowered, at which time each plant that produced pollen was self-pollinated. After approximately 3-4 weeks, ears were harvested and the kernels ($DH_1$ seeds) that formed on the treated $DH_0$ plants were counted to determine doubling efficiencies.

Doubling efficiencies (DE) were calculated under four different constraints, depending on the minimum number of kernels an ear had to produce in order to even be included in the calculation. $DE_{04}$ represents the portion of all the doubled $DH_0$ plants that produced a total of at least four seeds when all ears were considered. $DE_{20}$ represents the portion of all the doubled $DH_0$ plants that produced a total of at least 20 kernels when all ears were considered. Similarly, $DE_{30}$ represents the portion of doubled $DH_0$ plants that produced a total of at least 30 kernels when all ears were considered, and $DE_{50}$ represents the portion of doubled $DH_0$ plants that produced a total of at least 50 kernels when all ears were considered.

Furthermore, the above doubling efficiencies were calculated once by considering only the kernels that formed on the primary ear of each plant ($Ear_1$), once by considering only the kernels that formed on the primary and secondary ear of each plant ($Ear_2$), once by considering only the kernels that formed on the primary, secondary, and tertiary ear of each plant ($Ear_3$), and finally by considering all the kernels that formed on all the ears of each plant ($Ear_{all}$).

Comparison of doubling efficiencies produced by co-dominant ear induction at various minimum kernel/plant thresholds. Subscripts represent the minimum number of kernels a plant had to produce in order to be considered in the calculation of DE.

| | $DE_{04}$ | $DE_{20}$ | $DE_{30}$ | $DE_{50}$ |
|---|---|---|---|---|
| $Ear_1$ | 71% | 37% | 26% | 23% |
| $Ear_2$ | 76% | 59% | 47% | 36% |
| $Ear_3$ | 76% | 65% | 58% | 50% |
| $Ear_{All}$ | 76% | 68% | 58% | 52% |

These results reveal that greater doubling efficiencies were obtained whenever the kernels of co-dominant ears were included. This relationship becomes even more apparent when minimum yield constraints for an ear to be included were applied. For $DE_{20}$, $DE_{30}$, and $DE_{50}$, including the kernels produced by all ears on each plant approximately doubled the DE over the $EAR_1$ DE in each case. This demonstrates the utility of these methods over wide range of minimum yield constraints.

These results reveal that a user of these methods should experience more consistent DE among a variety of different minimum yield constraints as compared to methods currently known in the art. While the $Ear_1$ DE dropped by almost half between $DE_{04}$ and $DE_{20}$ (from 71% to 37%), including only one additional ear ($Ear_2$) resulted in only a 22% reduction in DE between $DE_{04}$ and $DE_{20}$ (from 76% to 59%). This reduction between $DE_{04}$ and $DE_{20}$ was even less for $Ear_3$ and $Ear_{all}$.

Since DE is a factor of the number of ears bearing a certain number of seeds recovered from an individual plant at a given generation, a user of these methods can expect to recover greater numbers of seed from a given plant, and thus will be more likely to recover at least a minimum number of seeds from any particular cross than one using methods that are presently known in the art. Thus, users of these methods will be more successful at recovering the minimum number of seeds from a cross in a single generation that is necessary to efficiently test that population to make accurate advancement decisions in a breeding program and bring products to market faster. A user of these methods will also be better able to predict DE across different minimum yield thresholds and thus be better able to anticipate recourse allocation among the populations derived from at least one induction cross.

Example 3. The Induction of co-Dominant Ears Improves the DE of Diverse Germplasms Two F1 hybrid-derived (one male and one female) haploid populations (referred to herein as H1 and H2) and two inbred-derived haploid lines (male Germplasm B and female Germplasm A) were tested in this experiment. Seven days after planting, several dozen seedlings from each group were removed from the soil and subjected to a bulk colchicine-based chromosome doubling treatment as described above. After the chromosome doubling treatment, seedlings were transplanted to soil and tended in a greenhouse at standard maize growing conditions. When the seedlings had reached approximately the V7 or V8 stage (approximately 29 days after doubling under the growing conditions used), the seedlings were subjected to co-dominant ear induction treatment comprising 60 mL of 2.5% PBZ added to the soil surrounding the base of each stem.

The seedlings were then tended in standard greenhouse maize growing conditions until they flowered, at which time each plant that produced pollen was self-pollinated and then left undisturbed to await fertilization and kernel production. After approximately 2-3 weeks, ears were harvested and the kernels that formed on them ($DH_1$) were counted to determine doubling efficiencies.

Doubling efficiencies (DE) were calculated under the different constraints described in the previous example to generate values for $DE_{04}$, $DE_{20}$, $DE_{30}$, and $DE_{50}$ for each of the four genotypes. Furthermore, the above doubling efficiencies were calculated once by considering only the kernels that formed on the primary ear of each plant ($Ear_1$), once by considering only the kernels that formed on the primary and secondary ear of each plant ($Ear_2$), once by considering only the kernels that formed on the primary, secondary, and tertiary ear of each plant ($Ear_3$), and finally by considering all the kernels that formed on all the ears of each plant ($Ear_{all}$).

TABLE 3

Doubling efficiencies of four germplasms depending on whether only the primary ear was harvested ($Ear_1$) or all ears were harvested ($Ear_{all}$).

| | $Ear_1$ | | | | $Ear_{all}$ | | | |
|---|---|---|---|---|---|---|---|---|
| | $DE_{04}$ | $DE_{20}$ | $DE_{30}$ | $DE_{50}$ | $DE_{04}$ | $DE_{20}$ | $DE_{30}$ | $DE_{50}$ |
| Control | | | | | | | | |
| A | 72.9 | 60.7 | 48.6 | 48.6 | 81 | 76.9 | 76.9 | 64.8 |
| A | 64.6 | 37.4 | 30.6 | 23.8 | 81.6 | 71.4 | 71.4 | 64.6 |
| Control | | | | | | | | |
| B | 64.8 | 44.5 | 40.5 | 32.4 | 68.8 | 56.7 | 56.7 | 44.5 |
| B | 56.7 | 40.5 | 40.5 | 40.5 | 68.8 | 48.6 | 44.5 | 44.5 |

Table 3 reveals that these methods can be used with a wide diversity of germplasms, including among inbred lines from different heterotic groups and among hybrids derived from inbreds from different heterotic groups. It also reveals that across all germplasms and minimum yield thresholds, the $Ear_{all}$ results always outperformed the $Ear_1$ results, demonstrating that a user of these methods can expect to improve DE by including the kernels produced by all additional co-dominant ears. These results suggest that these methods could be adapted for use with substantially any genotype or germplasm of maize.

Example 4. Co-Dominant Ear Induction Combines the Doubling Odds of Multiple Axillary Meristems to Improve DE and Seed Set When the $DH_1$ ears were harvested in the experiment described in Example 3, four $DH_0$ plants selected randomly from each germplasm were subjected to further scrutiny comprising recording of the approximate number of seeds produced from the first 3 co-dominant ears for each plant. FIG. 1 shows the first three ears that were harvested from each of these four plants and that figure is also represented in Table 4, below. In Table 4, ears are assigned to one of 4 categories, depending on the approximate number of seeds they produced: Class A ears produced approximately 50 seeds, Class B ears produced approximately 20-49 seeds, Class C ears produced approximately 1-20 seeds, and Class 0 ears produced zero seeds. Two plants failed to produce a third ear.

TABLE 4

Ears classified by the number of $DH_1$ seed they produced. "—" represents a situation where a third ear was not formed by the plant. The highest-yielding ear for each plant-germplasm combination is bolded in order to facilitate comparisons.

| | Plant # | | | | | | | | | | | |
|---|---|---|---|---|---|---|---|---|---|---|---|---|
| | 1 | | | 2 | | | 3 | | | 4 | | |
| | Ear # | | | | | | | | | | | |
| | $1^{st}$ | $2^{nd}$ | $3^{rd}$ | $1^{st}$ | $2^{nd}$ | $3^{rd}$ | $1^{st}$ | $2^{nd}$ | 3 | $1^{st}$ | $2^{nd}$ | $3^{rd}$ |
| Control | | | | | | | | | | | | |
| A | B | A | — | C | B | C | A | C | 0 | B | B | 0 |
| A | C | B | C | C | A | C | C | C | B | A | C | 0 |
| Control | | | | | | | | | | | | |
| B | C | C | B | A | A | 0 | A | 0 | C | B | B | C |
| B | C | A | — | B | C | C | C | A | C | C | A | C |

These results reveal the discovery that different co-dominant ears have different doubling potentials. It also reveals the surprising result that the highest-yielding ears may not be the first ear, or even the first or second ear. For example, the second ear yielded the most seeds on Plant 1 from the Control A, Germplasm A and Germplasm B germplasms. For Plant 1 of Control B and Plant 3 of Germplasm A, the third ear exhibited the greatest doubling potential.

This experiment also reveals the surprising result that haploid plants subjected to a co-dominant ear induction treatment will invest more resources developing ears that have been successfully doubled and that are capable of producing viable diploid offspring, independent of the relative position of the ear on the stem. Development of haploid ears that are not doubled, and thus are unlikely to produce seed, appears to be arrested. For example, the ears producing no seed, or very few (1-4) seeds, on plant #2 and plant #3 of the H2 germplasm appear to have been arrested while the plant clearly continued to invest resources into developing the ears that did produce seed. This suggests that when development of an induced co-dominant ear growing on $DH_0$ plant is arrested it is because the ear was not doubled and not because of the ear's position on the stem. Thus, an induced co-dominant and successfully-doubled ear growing from a lower node is more likely to follow the development schedule expected of a codominant ear than an ear growing higher up the stem that is not successfully doubled.

Example 5. Co-Dominant Ear Induction Dramatically Increases Seed Production in Diploids Seeds of maize inbred lines Germplasm A and LH244 were planted in soil, germinated, and then transplanted to 10-inch pots after approximately one week, one seedling per pot. The plants were subjected to a co-dominant ear induction treatment at the V8 stage comprising drenching the soil surrounding the roots of each plant with 50 mL of a 2.5% PBZ solution (v/v; 0.4% of active ingredient). The plants were tended in a greenhouse until sexual maturity, then they were self-pollinated. When seed set had completed, the number of co-dominant ears, and the total number of kernels, produced by each plant were counted. Control plants for each germplasm were processed in the same way as the treated groups, except that the control plants were not subjected to the co-dominant ear induction treatment.

TABLE 5

Average number of ears per plant and average total kernels per plant recovered from two genotypes subjected to a co-dominant ear induction treatment vs. a control treatment.

| | Ave. Ears Per Plant | | Ave. Total Kernels Per Plant | |
|---|---|---|---|---|
| | Treated | Control | Treated | Control |
| Germplasm A | 8 | 3.5 | 1677 | 746 |
| LH244 | 5.1 | 2.5 | 1126 | 557 |

Table 5 reveals the surprising result that it is possible to dramatically increase the average total kernels per plant produced from two different inbred lines by subjecting the plants to a co-dominant ear induction treatment. Both germplasms, very diverse from one another, responded to the co-dominant ear induction treatment by more than doubling the average total kernels per plant and the average ears per plant. Furthermore, all ears recorded from the treated groups in Table 5 were co-dominant.

Figure 2:
FIG. 2 shows eight numbered maize co-dominant ears growing from a single plant that was treated with a plant growth regulator.

A representative example of a Germplasm A plant that produced 8 ears following treatment with these methods is shown in FIG. 2.

Although the control plants produced multiple ears, they produced no co-dominant ears; only the primary ears on the control plants nicked well enough to produce any seed.

Example 6. Tiller Induction Dramatically Increases Seed Production in Diploids

Diploid maize plants of a common inbred line were subjected to a tiller induction treatment comprising drenching the soil surrounding the roots with 100 mL of a 2.5% PBZ solution (v/v; 0.4% of active ingredient) approximately one week after germination and then allowed to grow to sexual maturity in 10-inch pots a greenhouse. A control group of plants were grown under identical circumstances except that they were not subjected to the tiller induction treatment.

Figure 3:
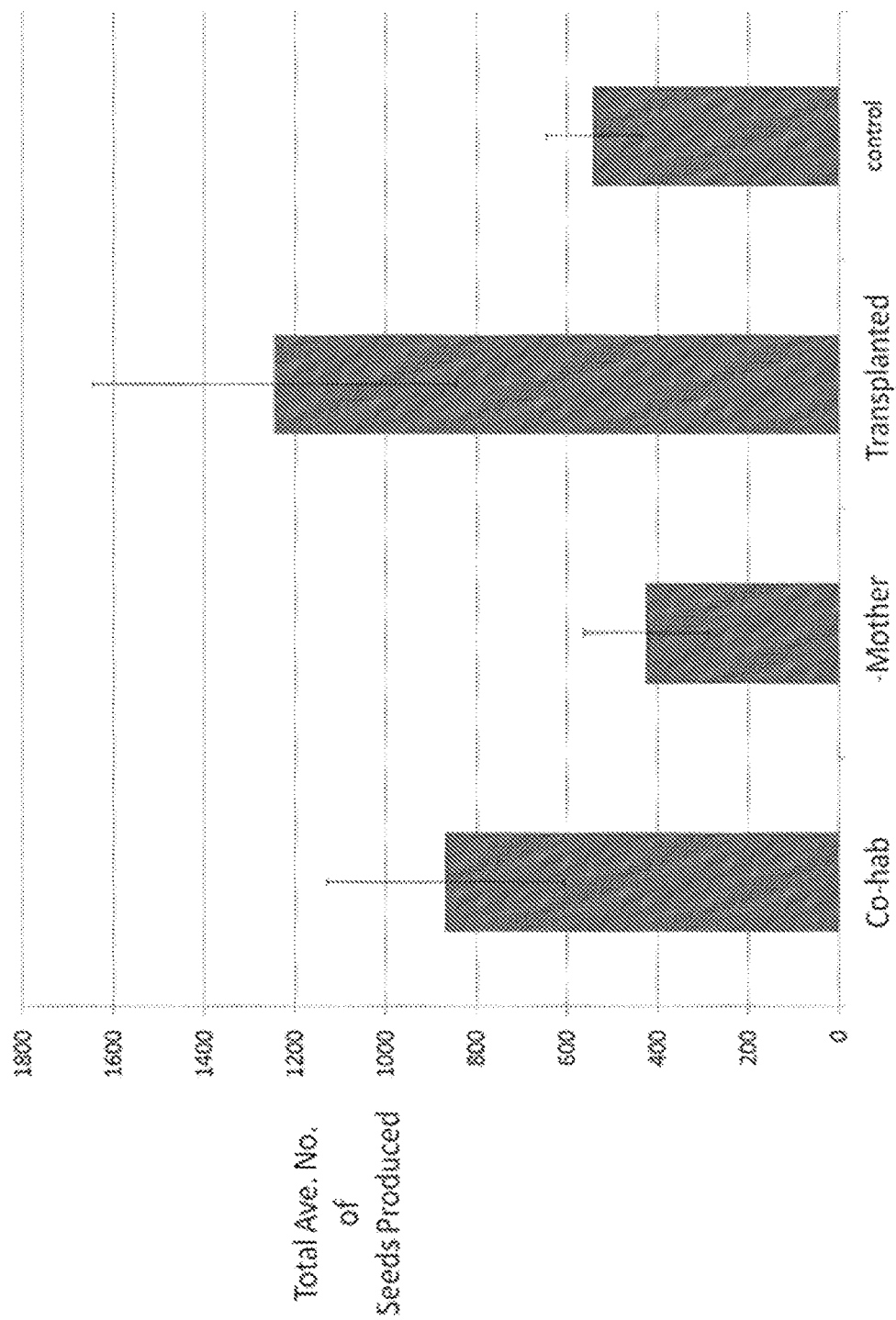
FIG. 3 shows the average total number of seeds produced from tillers derived from the same mother plant that was subjected to a tiller induction treatment.

The GA inhibitor resulted in the mother plants expressing shortened internodes, and induced the mother plants to produce tillers. Three treatment groups were then formed from the tillers: tillers of the "Co-hab" treatment were allowed to continue growing in the same pot with the mother plant; those of the "-Mother" treatment also remained in the same pot, but the mother plant was removed from the pot; and those of the "Transplanted" treatment group were transplanted from the pot containing the mother plant into separate 10-inch pots, one plant per pot. Any naturally-occurring tillers produced by the control group were allowed to grow in the same pot as the mother plant, similar to the co-hab treatment. All plants were allowed to grow to sexual maturity and self-pollinated when silks and tassels formed. When seed set was complete, the average total number of seeds produced by all plants deriving from the same mother plant seed were counted and plotted in FIG. 3.

These results reveal that it is possible to dramatically increase the average total seeds per plant by subjecting plants to a tiller-induction treatment, evidenced by the transplanted treatment group producing more than twice the number of seeds as the control group. It also reveals that the best recovery of seeds occurred when tillers were transplanted away from the mother plant.

Example 7. The Tiller-Induction Method and Doubling Haploid Plants

A haploid mother plant will be subjected to doubling treatment and thereafter planted in a pot, the soil surrounding the roots drenched with 100 mL of 2.5% of paclobutrazol, and then tended standard maize greenhouse growing conditions for several days. The GA inhibitor will result in the mother plant expressing shortened internodes and increased tiller production. One of the resulting daughter tiller plants can be separated from the mother plant, transplanted into a separate pot, and grown via standard greenhouse management procedures to eventually recover a daughter plant with normal haploid morphology. This daughter plant will produce abundant pollen and a robust ear that nicks well and yield several dozen $DH_1$ seeds when selfed.

It is anticipated that that these tiller induction methods can be used in conjunction with DH methods to dramatically increase the likelihood of recovering $DH_1$ seed from a given $DH_0$ mother plant. It is anticipated that a user can induce a $DH_0$ plant to form doubled-haploid tillers, each generating ears that nick well with their respective tassels to produce dozens of doubled haploid seed. It is expected that one could use these methods to generate as many tillers as are necessary to obtain a quantity of $DH_1$ seed desired by the user.

Example 8. Multibud Induction can be Used in Conjunction with DH Methods to Rapidly Generate Plants Homozygous for Multiple Traits Seeds of a diploid maize plant were surface sterilized comprising immersion using standard methods of the art and then germinated in vitro in growth media. One of the resulting seedlings was dissected from its seed two days after germination (embryo axis method). The dissected axis was then subjected to a multibud induction treatment comprising transfer to fresh multibud induction media containing cytokinin in the form of 10 mg/L BAP. After seven days in the multibud bud induction media, the treated seedlings were transferred back to a hormone-free regeneration media.

After approximately twenty days, induced multibuds could be seen growing from the nodal regions of the stem. These multibuds were dissected from the mother plant and transferred to rooting media comprising IBA and IAA. After approximately one week, the multibud-derived plants were transplanted into 10 inch pots and allowed to grow in a greenhouse until it was clear that each autonomously-growing multibud-derived shoot had formed ears and tassels that nicked. Each ear was then pollinated from the tassel growing in the same pot and then all plants were allowed to grow in greenhouse conditions until seed set. In each case, the multibud-derived plants produced ears that bore dozens of seed each.

This example reveals that multibuds induced from a single mother plant can be cultured to produce fertile ears and tassels that nick well and produce excellent seed set. It is thus anticipated that a user of these methods can use multibuds to increase the likelihood of recovering at least one seed from a given plant.

In one embodiment, the user induces a mother haploid plant subjected to chromosome doubling to a multibud induction treatment to produce multiple doubled-haploid buds. These multibuds can be cultured to produce DH seed.

In another embodiment, the user subjects a diploid plant containing at least one desired trait in a heterozygous state to a multibud induction treatment to produce several diploid multibuds. These multibuds are separated from the mother plant and grown to produce tassels and ears. Next, the user pollinates the multibud-derived diploid plants with a maternal haploid inducer to generate haploid offspring, at least one of which contains the desired allele of the trait. The haploid offspring can then be subjected to a colchicine doubling treatment to produce a doubled haploid plant containing the desired trait in the homozygous condition. This method has the potential to dramatically increase the efficiency of creating a plant that is homozygous for more than one trait as the user can induce the formation of many new inflorescences from a single mother plant, thereby increasing the likelihood of producing an egg containing the desired traits in a homozygous state from each mother plant. Once a haploid plant containing the desired traits in the homozygous condition is generated, the user subjects the plant to a chromosome doubling treatment to recover a homozygous diploid.

Example 9. Manipulation of Single Plant Kernel Yield and Number of Ears Per Plant in Corn This example describes a method for manipulating yield in corn using a chemistry applied to the roots of corn plants. This application resulted in the induction of multiple tillers per plant which when transplanted and grown to maturity yielded increased number of ears with viable seed set and increased single plant kernel return (yield).

LH244 corn seed was planted in six pack cells and germinated under standard greenhouse conditions using a 16 hr day and 8 hr night cycle and temperatures of 86° F./68° F. At ten days post germination a total of forty seedlings were transplanted into eight litre (L) pots and the resulting plants were randomized in two short rows. At about fourteen days post germination (plants were at the V3-V4 stage) a 50 mL solution of 2.5% (5 mg/plant) Paczol (active ingredient: 0.4% Paclobutrazole; Olympic Horticulture) was applied to thirty of the forty plants to the soil at the base of each pot. Ten plants (control group) remained untreated. Plants were subsequently grouped into four groups of ten plants each and received different treatments to assess the highest yield potential as described in Table 6. The application of Paczol to the roots of V3-V4 seedlings resulted in the production of several (1-3) tillers per plant. For the first group of 10 plants (collectively described as Treatment #1) both main stem and axillary tillers were allowed to grow and all ears on both the main stem and the axillary tillers were pollinated, including cross pollination between the main stem and the axillary tillers. In the group receiving Treatment #2 the main stem was decapitated fourteen days after the Paczol application and the axillary tillers were allowed to develop and pollinate without the presence of the main stem. In the group receiving Treatment #3 all axillary tillers and their roots were removed at thirty days after Paczol application and transplanted into their own separate pots. Transplanted tillers were placed in a humidity dome until established (approximately 10-13 days). Main stem and tillers were then pollinated. When not enough pollen was produced by the tillers the main stem pollen was used to pollinate the transplanted tillers. The final treatment consisted of the control group which did not receive the Paczol application. In this case, all ears were pollinated including, when present, the tiller ears.

TABLE 6

Number of kernels per ear in treatment groups of plants after Paczol application.

Application: Paczol 50 mL at V3 — CORN × PACZOL

TREATMENT #1 Main branch and Tillers left untouched and all were pollinated

| Plant | Kernels/Ear #1 | Kernels/Ear #2 | Kernels/Ear #3 | Kernels/Ear #4 | Kernels/Ear #5 | Kernels/Ear #6 | Kernels/Ear #7 |
|---|---|---|---|---|---|---|---|
| 1 | 470 | 60 | 50 | | | | |
| 2 | 403 | 63 | 12 | | | | |
| 3 | 530 | 376 | 89 | 5 | 5 | | |
| 4 | 418 | 482 | 389 | 14 | 16 | | |
| 5 | 473 | 422 | 235 | 27 | 40 | | |
| 6 | 403 | 370 | 56 | | | | |
| 7 | 425 | 413 | 44 | | | | |
| 8 | 321 | 263 | 72 | | | | |
| 9 | 443 | 350 | 70 | | | | |
| 10 | 409 | 426 | 40 | | | | |

TREATMENT #2 Main branch decapitated and tillers allowed to grow and pollinate (including main ear)

| Plant | Kernels/Ear #1 | Kernels/Ear #2 | Kernels/Ear #3 | Kernels/Ear #4 | Kernels/Ear #5 | Kernels/Ear #6 | Kernels/Ear #7 |
|---|---|---|---|---|---|---|---|
| 1 | 426 | 13 | | | | | |
| 2 | 438 | | | | | | |
| 3 | 365 | 14 | | | | | |
| 4 | 300 | | | | | | |
| 5 | 503 | 75 | 10 | | | | |
| 6 | 330 | 22 | | | | | |
| 7 | 353 | 102 | | | | | |
| 8 | 504 | 127 | 12 | | | | |
| 9 | 420 | 41 | 33 | | | | |
| 10 | 173 | | | | | | |

TREATMENT #3 Tillers Transplanted and pollinated independently of main branch

| Plant | Kernels/Ear #1 | Kernels/Ear #2 | Kernels/Ear #3 | Kernels/Ear #4 | Kernels/Ear #5 | Kernels/Ear #6 | Kernels/Ear #7 |
|---|---|---|---|---|---|---|---|
| 1 | 390 | 491 | | | | | |
| 2 | 340 | 471 | 275 | 233 | 73 | | |
| 3 | 394 | 409 | 341 | 222 | 92 | 70 | 46 |
| 4 | 481 | 521 | 414 | 33 | | | |
| 5 | 615 | 387 | 50 | 28 | | | |
| 6 | 433 | 334 | 423 | 210 | 391 | | |
| 7 | 442 | 444 | 412 | 81 | 36 | | |
| 8 | 414 | 484 | 236 | 114 | 59 | 45 | 90 |
| 9 | 436 | 441 | 101 | 48 | | | |
| 10 | 390 | 23 | | | | | |

Control: Keep main branch and tillers together and pollinate all

| Plant | Kernels/Ear #1 | Kernels/Ear #2 | Kernels/Ear #3 | Kernels/Ear #4 | Kernels/Ear #5 | Kernels/Ear #6 | Kernels/Ear #7 |
|---|---|---|---|---|---|---|---|
| 1 | 426 | | | | | | |
| 2 | 395 | 313 | | | | | |
| 3 | 0 | | | | | | |
| 4 | 428 | 101 | | | | | |
| 5 | 447 | | | | | | |
| 6 | 0 | | | | | | |
| 7 | 477 | 105 | | | | | |
| 8 | 464 | | | | | | |

TABLE 6-continued

Number of kernels per ear in treatment groups of plants after Paczol application.

| 9  | 490 | 17  |
|----|-----|-----|
| 10 | 508 | 166 |

Figure 4:
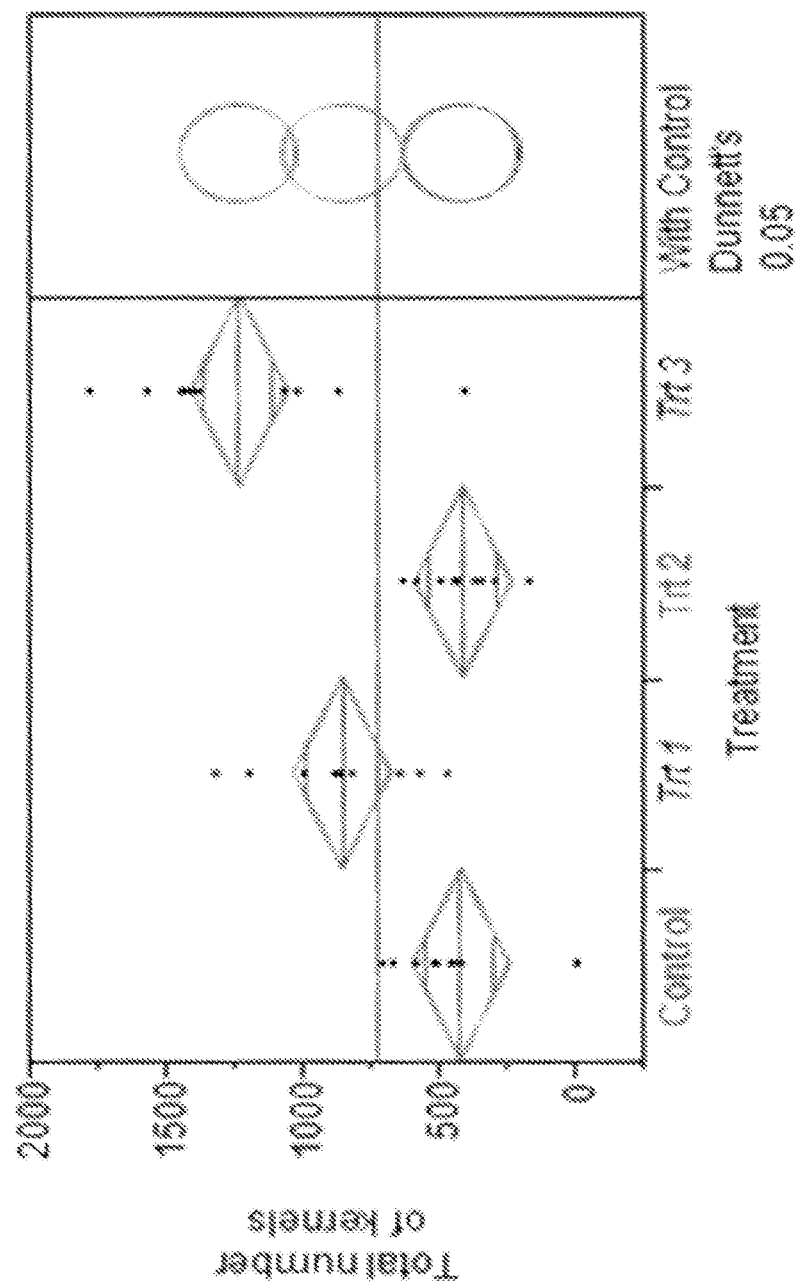
FIG. 4 shows one-way statistical analysis on the total number of kernels per plant for the treatments described.

Treatment #3 which consisted of transplanting the axillary tillers from the main branch and propagating them independently, resulted in the largest number of kernels being produced. This data is also illustrated in FIG. 4.

Example 10. Manipulation of Vegetative and Reproductive Growth in Wheat Leads to Increases in Total Head Number, Seed Weight, Grain Weight and Total Dry Weight Mass at Harvest Compared to the Untreated Control This example describes a method for manipulating vegetative and reproductive growth in wheat using a chemistry applied to the roots of the plants. This application resulted in the induction of multiple tillers per plant and altered biomass and length of the main branch, and biomass and length of the axillary tillers.

Figure 5:
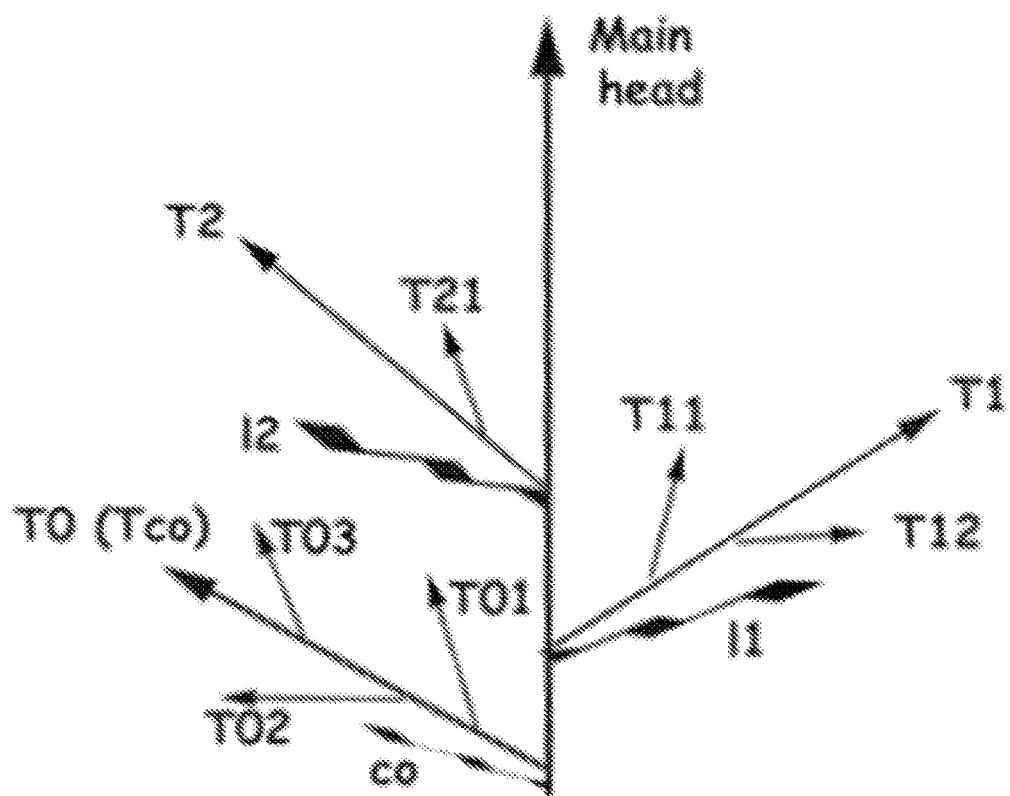
FIG. 5 is an illustration of tiller development and location on wheat plants.
Figure 6:
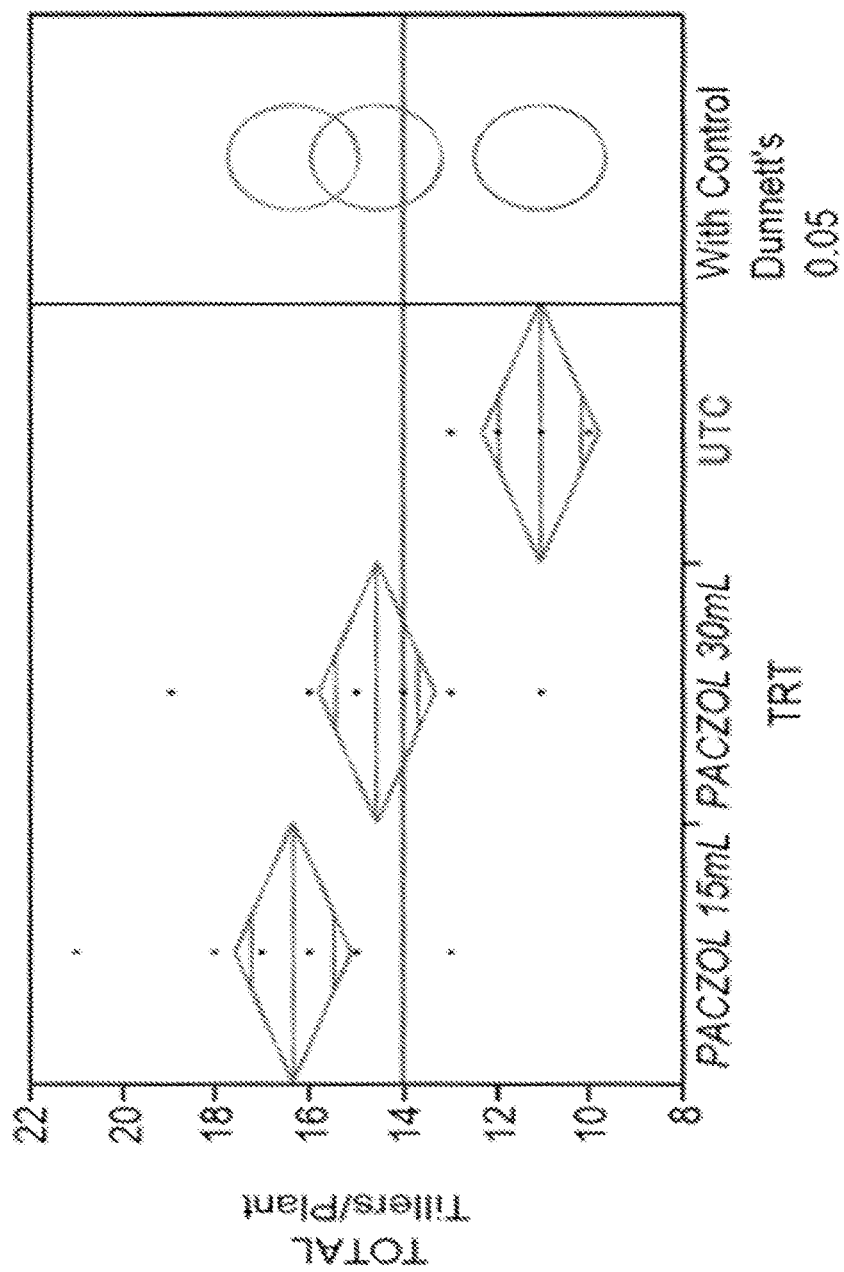
FIG. 6 shows one-way analysis of total tiller per plant at 20 day after treatment in control and Paczol treated plants (15 mL at V3 stage or 30 mL at V8 stage).
Figure 7A:
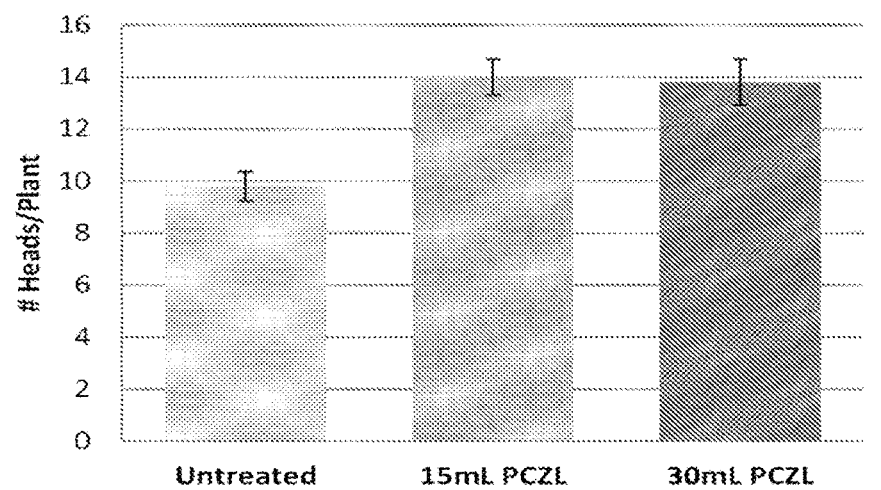
FIG. 7A-D show that chemical treatment of wheat seedlings with Paczol improves reproductive traits such as the number of heads per plant (A), the number of seed per plant (B), the amount of seed per plant (grams seed/plant, C) and the total dry matter per plant (D).
Figure 7B:
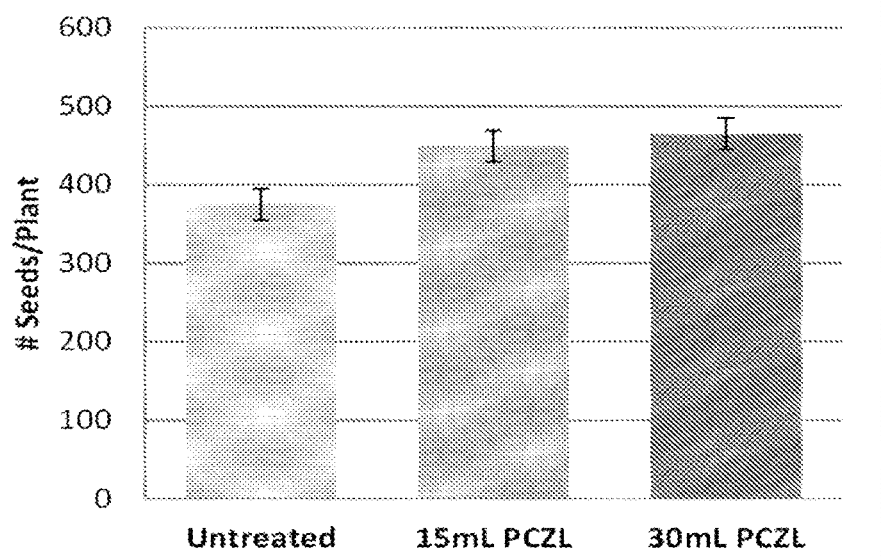
Figure 7C:
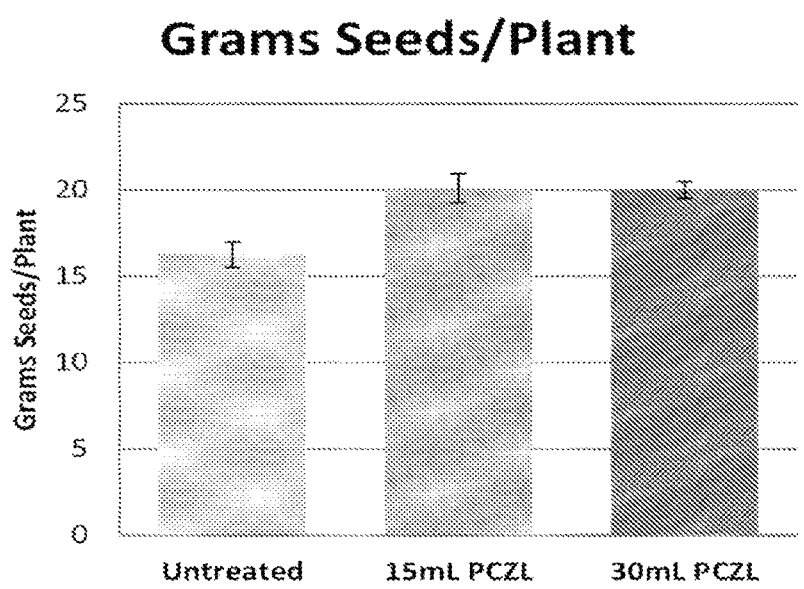
Figure 7D:
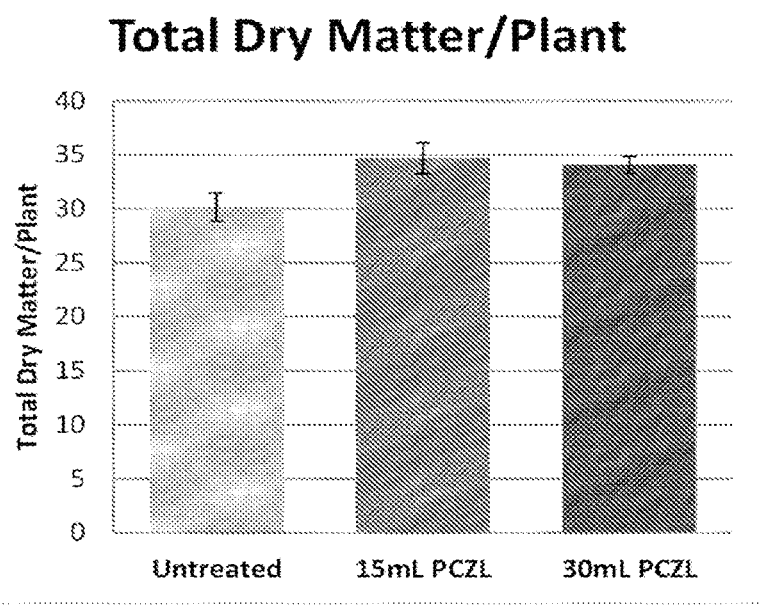

Wheat var. Samson was planted in six pack cells and germinated under standard greenhouse conditions using a 16 hr day and 8 hr night cycle and temperatures of 86° F./68° F. At ten days post germination a total of thirty seedlings were transplanted into 2.7 litre (L) pots and the resulting plants were randomized in two short rows. At fifteen days post germination (wheat seedlings were at the V3-V4 stage) a onetime treatment of a 2.5% solution of Paczol (active ingredient 0.4% Paclobutrazole, Olympic Horticulture) was applied to the soil at the base of the emerging plant. Two treatments were tested on groups of ten plants per treatment. An untreated control was also present. The first treatment consisted of an application of fifteen milliliter (mL) of a 2.5% (1.5 mg/plant) solution of Paczol applied to the base of the emerging plant. The second treatment was thirty mL of a 2.5% (3.0 mg/plant) solution of Paczol applied to the base of the emerging plant. Plants were not watered for four days following treatment. Subsequent hand watering of the plants occurred on an as needed basis with the soil allowed to dry completely between watering. Tillers were considered emerged when they became fully visible or when their youngest leaf tip surpassed the ligule of the subtending leaf as illustrated in the diagram in FIG. 5. At the completion of the study ten plants per treatment were processed for mainstem biomass, mainstem length, tiller biomass, tiller number and tiller length. Additional groupings of ten plants were allowed to reach maturity and assessed for total dry matter, head number, seed number and grain weight. The results of the total number of tillers are summarized in Table 7. Additionally, FIG. 6 provides the statistical analysis of the number of primary and secondary tillers grouped by length and at the end of the experiment (Day 20). FIG. 7A-D provides the analysis of the key reproductive traits such as the number of heads per plant, number of seeds per plant, grams of seeds per plant and total dry matter per plant, all of which were significantly increased over the untreated control. In general, Paczol treatment of wheat appeared to delay maturity of the plants by about five days with many late emerging tillers compared to the untreated control as well as reduce the stature of the treated plants compared to untreated.

TABLE 7

Number of Primary and Secondary Tillers in Wheat Plants treated with Paczol.

| Treatment | Plant WT (g) | Total # of Primary Tillers | Total # of Secondary Tillers | WHOLE PLANT TILLERS TOTAL |
|---|---|---|---|---|
| Untreated Control | | | | |
| 1  | 17.3 | 8  | 3 | 11 |
| 2  | 23.7 | 9  | 2 | 11 |
| 3  | 19.6 | 10 | 0 | 10 |
| 4  | 22.9 | 9  | 3 | 12 |
| 5  | 21.1 | 8  | 3 | 11 |
| 6  | 22.3 | 9  | 1 | 10 |
| 7  | 22.2 | 8  | 2 | 10 |
| 8  | 26.1 | 12 | 1 | 13 |
| 9  | 18.9 | 7  | 4 | 11 |
| 10 | 21.4 | 9  | 3 | 12 |
|    | Avg 21.55 | Avg 8.9 | Avg 2.2 | Avg 11.1 |
| PACZOL 15 mL | | | | |
| 1  | 20.1 | 14 | 3 | 17 |
| 2  | 22.6 | 18 | 3 | 21 |
| 3  | 17.4 | 9  | 4 | 13 |
| 4  | 22.3 | 13 | 4 | 17 |
| 5  | 22.1 | 13 | 5 | 18 |
| 6  | 21.5 | 14 | 4 | 18 |
| 7  | 20.5 | 13 | 3 | 16 |
| 8  | 19.8 | 11 | 4 | 15 |
| 9  | 17.5 | 10 | 3 | 13 |
| 10 | 22.4 | 12 | 4 | 16 |
|    | Avg 20.62 | Avg 12.7 | Avg 3.7 | Avg 16.4 |
|    |   |   |   | Increase: 47.7% |
| PACZOL 30 mL | | | | |
| 1  | 19.7 | 10 | 6 | 16 |
| 2  | 24.3 | 14 | 5 | 19 |
| 3  | 22.6 | 13 | 2 | 15 |
| 4  | 22.5 | 12 | 2 | 14 |
| 5  | 19.4 | 11 | 3 | 14 |
| 6  | 19.4 | 12 | 3 | 15 |
| 7  | 21.4 | 13 | 2 | 15 |
| 8  | 16   | 10 | 3 | 13 |
| 9  | 17.8 | 12 | 2 | 14 |
| 10 | 16.1 | 9  | 2 | 11 |
|    | Avg 19.92 | Avg 11.6 | 3 | Avg 14.6 |
|    |   |   |   | Increase: 31.5% |

The two Paczol treatments resulted in an average increase of 47.7% (15 mL application) and 31.5% (30 mL application) in tillers respectively.

Example 11. Manipulation of Vegetative and Reproductive Growth in Corn at Different Distinct Developmental Stage Leads to an Increase in Kernel Number and Improved Maleness of the Treated Plants This example illustrates further manipulation of corn vegetative and reproductive growth by use of a chemical treatment at two separate developmental stages. Further, this example illustrates the use of whole plant bags to facilitate auto-selfing as opposed to hand pollinations which are the traditional method employed in greenhouse grown corn.

Corn seedlings (Germplasm C) were grown in the greenhouse using the same conditions as described in Example 1. At approximately 14-16 day after transplanting (V3 stage) twenty corn seedling plants were treated with fifty mL each of a 2.5% solution of Paczol applied directly to the soil at the base of the plant. An additional twenty plants were treated at twenty eight day after transplanting (V8 stage) with one hundred mL of a 5% solution of Paczol. An untreated control group consisted of ten plants which were further pollinated by hand as is customary procedure (ear and tassel bagged separately and hand pollinated). The plants that had received the Paczol treatment at V3 and V8 stage were further separated into two groups. One group in each treatment was hand pollinated (as in the control group). For the other set of plants in each treatment group a whole plant bag was placed over each plant at the beginning of pollen formation and the plants were allowed to self-fertilize. Plants were monitored for height, tiller number and male/female gender development, total number of axillary tillers per plant, total number of tassels developed (on main or axillary tillers), the number of days the pollen shed lasted and finally the number of kernels produced. The main results are summarized in Table 8.

TABLE 8

Measurements taken in corn seedlings treated with Paczol at V3 or V8 stage

| Treatment | Plant Height | Tiller # and Male/Female Gender | Total Tillers/Plant | Tassel # (tiller + main) | Days Pollen Shed Duration | Kernels |
|---|---|---|---|---|---|---|
| UTC 1 | 61 | 0 | 0 | 1 | 6 | 146 |
| UTC 2 | 53 | 0 | 0 | 1 | 7 | 405 |
| UTC 3 | 60.5 | 0 | 0 | 1 | 5 | 390 |
| UTC 4 | 59 | 0 | 0 | 1 | 5 | 187 |
| UTC 5 | 61.5 | 0 | 0 | 1 | 6 | 380 |
| UTC 6 | 70.5 | 0 | 0 | 1 | 6 | 404 |
| UTC 7 | 62 | 0 | 0 | 1 | 6 | 402 |
| UTC 8 | 64 | 0 | 0 | 1 | 7 | 219 |
| UTC 9 | 63.5 | 0 | 0 | 1 | 6 | 192 |
| | | | | | | Avg = 303 |
| V3 Hand 1 | 46 | 2M | 2 | 3 | 17 | 742 |
| V3 Hand 2 | 43 | 2M1F | 3 | 3 | 17 | 479 |
| V3 Hand 3 | 43 | 2M1F | 3 | 3 | 18 | 604 |
| V3 Hand 4 | 45 | 2M | 2 | 3 | 17 | 416 |
| V3 Hand 5 | 44.5 | 2M1F | 3 | 3 | 20 | 262 |
| V3 Hand 6 | 42.5 | 2M1F | 3 | 3 | 20 | 409 |
| V3 Hand 7 | 47 | 2M | 2 | 3 | 17 | 504 |
| V3 Hand 8 | 43.5 | 2M2F | 4 | 3 | 19 | 558 |
| | | | | | | Avg = 497 |
| V3 Auto 1 | 41 | 2M | 2 | 3 | 18 | 665 |
| V3 Auto 2 | 41 | 2M | 2 | 3 | 17 | 441 |
| V3 Auto 3 | 41 | 2M1F | 3 | 3 | 18 | 411 |
| V3 Auto 4 | 42.5 | 2M | 2 | 3 | 19 | 569 |
| V3 Auto 5 | 43 | 2M | 2 | 3 | 19 | 1051 |
| V3 Auto 6 | 46 | 2M1F | 3 | 3 | 20 | 283 |
| V3 Auto 7 | 40 | 3M1F | 4 | 4 | 17 | 809 |
| V3 Auto 8 | 41 | 2M | 2 | 3 | 18 | 612 |
| | | | | | | Avg = 605 |
| V8 Hand 1 | 36 | 2F | 2 | 1 | 7 | 171 |
| V8 Hand 2 | 34 | 3F | 3 | 1 | 7 | 58 |
| V8 Hand 3 | 32 | 1M4F | 5 | 2 | 12 | 553 |
| V8 Hand 4 | 31 | 1M3F | 4 | 2 | 14 | 330 |
| V8 Hand 5 | 28 | 3F | 3 | 1 | 6 | 953 |
| V8 Hand 6 | 30.5 | 3F | 3 | 1 | 7 | 282 |
| V8 Hand 7 | 30 | 3F | 3 | 1 | 6 | 280 |
| V8 Hand 8 | 33.5 | 1M3F | 4 | 2 | 11 | 355 |
| V8 Hand 9 | 34 | 3F | 3 | 1 | 7 | 320 |
| V8 Hand 10 | 34.5 | 3F | 3 | 1 | 7 | 508 |
| | | | | | | Avg = 381 |
| V8 Auto 1 | 32 | 1M2F | 3 | 2 | 12 | 340 |
| V8 Auto 2 | 32 | 3F | 3 | 1 | 6 | 419 |
| V8 Auto 3 | 32 | 1M2F | 3 | 2 | 14 | 209 |
| V8 Auto 4 | 31 | 1M3F | 4 | 2 | 14 | 385 |
| V8 Auto 5 | 35 | 3F | 3 | 1 | 6 | 408 |
| V8 Auto 6 | 30 | 3F | 3 | 1 | 5 | 392 |
| V8 Auto 7 | 33 | 1M2F | 3 | 2 | 12 | 160 |
| V8 Auto 8 | 35.5 | 1M4F | 5 | 2 | 11 | 568 |
| | | | | | | Avg = 360 |

The average kernel number increased nearly 50% in the plants treated with Paczol at the V3 stage that were hand pollinated. Most significant, however, was the average kernel number increase for those V3-stage treated plants which were allowed to self-pollinate by virtue of having a whole plant bag placed over the canopy. These plants appeared to have more tassel developed as well as more tillers and on average doubled the yield of kernels per plant.

Figure 8:
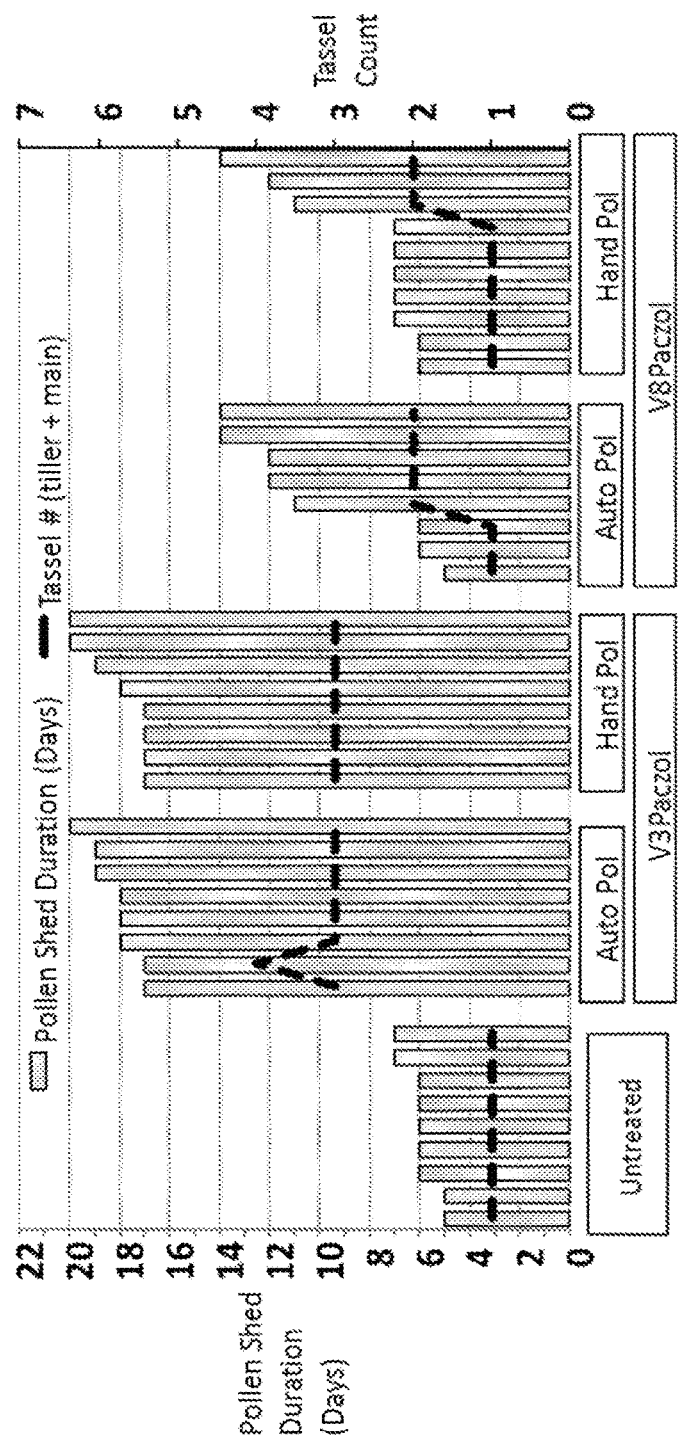
FIG. 8 shows that pollen shed duration and number of tassels on individual plants treated with Paczol at the V3- or V8-stage and then either hand pollinated or selfed by bagging (Auto Pol).

Additionally, the chemically treated plants appeared to have an extended pollen shed duration. This data is shown in FIG. 8.

Example 12. Manipulation of Gender, Tiller Number and Total Yield in Different Corn Germplasm The following example describes treatment in eleven different corn inbred germplasm lines by use of a chemistry at two separate developmental stages (V3 and V8). This example illustrates the application of chemical treatment in different germplasm and the yield results in these lines after hand or bag pollination.

Seeds for eleven corn inbred germplasm was planted in six-packs and grown in greenhouses under standard conditions as outlined in Example 1. At thirteen days after germination the seedlings for the eleven different germplasm (20 plants per germplasm) were transplanted into standard pots. At fifteen days after germination (V3 stage) a portion of the seedlings were treated with a 50 mL solution of 2-5% Paczol (4-10 mg/plant), while the remaining set of seedlings were treated at the V8-stage (twenty-eight day after germination). Table 9 shows the different germplasm used, the type of pollination (hand or auto-self via bag), the rate and number of plants treated in this experiment.

TABLE 9

Germplasm, treatment, rate and number of plants in testing eleven germplasm with chemistry.

| Unique Corn Germplasm | Treatment | Solution % | Volume Delivered to Each Pot | Paclobutrazol mg/plant | Treatment Code | Plants/TRT |
|---|---|---|---|---|---|---|
| A | Untreated Hand Pollinated | | | | UHP | 4 |
| B | Untreated Hand Polinated | | | | UHP | 4 |
| C | Untreated Hand Polinated | | | | UHP | 4 |
| D | Untreated Hand Polinated | | | | UHP | 4 |
| E | Untreated Hand Polinated | | | | UHP | 4 |
| F | Untreated Hand Polinated | | | | UHP | 4 |
| G | Untreated Hand Polinated | | | | UHP | 4 |
| H | Untreated Hand Polinated | | | | UHP | 4 |
| I | Untreated Hand Polinated | | | | UHP | 4 |
| J | Untreated Hand Polinated | | | | UHP | 4 |
| K | Untreated Hand Polinated | | | | UHP | 4 |
| A | 14DAP Chem Auto-self | 2% | 50 mL | 4 | 3HV | 4 |
| B | 14DAP Chem Auto-self | 3% | 50 mL | 6 | 3HV | 4 |
| C | 14DAP Chem Auto-self | 3% | 50 mL | 6 | 3HV | 4 |
| D | 14DAP Chem Auto-self | 3% | 50 mL | 6 | 3HV | 4 |
| E | 14DAP Chem Auto-self | 3% | 50 mL | 6 | 3HV | 4 |
| F | 14DAP Chem Auto-self | 3% | 50 mL | 6 | 3HV | 4 |
| G | 14DAP Chem Auto-self | 3% | 50 mL | 6 | 3HV | 4 |
| H | 14DAP Chem Auto-self | 3% | 50 mL | 6 | 3HV | 4 |
| I | 14DAP Chem Auto-self | 5% | 50 mL | 10 | 3HV | 4 |
| J | 14DAP Chem Auto-self | 5% | 50 mL | 10 | 3HV | 4 |
| K | 14DAP Chem Auto-self | 3% | 50 mL | 6 | 3HV | 4 |
| A | 14DAP Chem Auto-self | 6.25% | 16 mL | 4 | 3LV | 4 |
| B | 14DAP Chem Auto-self | 9.38% | 16 mL | 6 | 3LV | 4 |
| C | 14DAP Chem Auto-self | 9.38% | 16 mL | 6 | 3LV | 4 |
| D | 14DAP Chem Auto-self | 9.38% | 16 mL | 6 | 3LV | 4 |
| E | 14DAP Chem Auto-self | 9.38% | 16 mL | 6 | 3LV | 4 |
| F | 14DAP Chem Auto-self | 9.38% | 16 mL | 6 | 3LV | 4 |
| G | 14DAP Chem Auto-self | 9.38% | 16 mL | 6 | 3LV | 4 |
| H | 14DAP Chem Auto-self | 9.38% | 16 mL | 6 | 3LV | 4 |
| I | 14DAP Chem Auto-self | 15.63% | 16 mL | 10 | 3LV | 4 |
| J | 14DAP Chem Auto-self | 15.63% | 16 mL | 10 | 3LV | 4 |
| K | 14DAP Chem Auto-self | 9.38% | 16 mL | 6 | 3LV | 4 |
| A | 28DAP Chem Auto-self | 2% | 100 mL | 8 | 8HV | 4 |
| B | 28DAP Chem Auto-self | 4% | 100 mL | 16 | 8HV | 4 |
| C | 28DAP Chem Auto-self | 4% | 100 mL | 16 | 8HV | 4 |
| D | 28DAP Chem Auto-self | 4% | 100 mL | 16 | 8HV | 4 |
| E | 28DAP Chem Auto-self | 4% | 100 mL | 16 | 8HV | 4 |
| F | 28DAP Chem Auto-self | 4% | 100 mL | 16 | 8HV | 4 |
| G | 28DAP Chem Auto-self | 4% | 100 mL | 16 | 8HV | 4 |
| H | 28DAP Chem Auto-self | 4% | 100 mL | 16 | 8HV | 4 |
| I | 28DAP Chem Auto-self | 8% | 100 mL | 32 | 8HV | 4 |
| J | 28DAP Chem Auto-self | 8% | 100 mL | 32 | 8HV | 4 |
| K | 28DAP Chem Auto-self | 4% | 100 mL | 16 | 8HV | 4 |
| A | 28DAP Chem Auto-self | 13% | 16 mL | 8 | 8LV | 4 |
| B | 28DAP Chem Auto-self | 25% | 16 mL | 16 | 8LV | 4 |
| C | 28DAP Chem Auto-self | 25% | 16 mL | 16 | 8LV | 4 |
| D | 28DAP Chem Auto-self | 25% | 16 mL | 16 | 8LV | 4 |
| E | 28DAP Chem Auto-self | 25% | 16 mL | 16 | 8LV | 4 |
| F | 28DAP Chem Auto-self | 25% | 16 mL | 16 | 8LV | 4 |
| G | 28DAP Chem Auto-self | 25% | 16 mL | 16 | 8LV | 4 |
| H | 28DAP Chem Auto-self | 25% | 16 mL | 16 | 8LV | 4 |
| I | 28DAP Chem Auto-self | 50% | 16 mL | 32 | 8LV | 4 |
| J | 28DAP Chem Auto-self | 50% | 16 mL | 32 | 8LV | 4 |
| K | 28DAP Chem Auto-self | 25% | 16 mL | 16 | 8LV | 4 |

The results are summarized in Table 10 below. Results are also illustrated in graph format in FIGS. 10 and 11.

TABLE 10

Average number of kernels from the main stem and total number of kernels per plant (including tillers).

| Treatment | PBCZ mg/plant | Active Ingredient Paclobutrazol mg/plant (0.12 g ai per fluid oz or 4000 ppm) | Pedigree | Treatment Code | Avg Kernels from Main Stem | Avg Total Kernels Per Plant |
|---|---|---|---|---|---|---|
| Untreated Hand Polinated | | 0 | A | UHP | 317.75 | 317.75 |
| 14DAP Chem Auto-self | 4 | 4 | | 3HV | 330.50 | 351.00 |
| 14DAP Chem Auto-self | 4 | 4 | | 3LV | 352.25 | 515.75 |
| 28DAP Chem Auto-self | 8 | 8 | | 8HV | 337.00 | 345.75 |
| 28DAP Chem Auto-self | 8 | 8 | | 8LV | 366.50 | 413.00 |
| Untreated Hand Polinated | | 0 | B | UHP | 289.25 | 289.25 |
| 14DAP Chem Auto-self | 6 | 6 | | 3HV | 204.00 | 215.50 |
| 14DAP Chem Auto-self | 6 | 6 | | 3LV | 260.25 | 291.25 |
| 28DAP Chem Auto-self | 16 | 16 | | 8HV | 567.00 | 567.25 |
| 28DAP Chem Auto-self | 16 | 16 | | 8LV | 427.00 | 432.75 |
| Untreated Hand Polinated | | 0 | C | UHP | 60.00 | 60.00 |
| 14DAP Chem Auto-self | 6 | 6 | | 3HV | | |
| 14DAP Chem Auto-self | 6 | 6 | | 3LV | 291.50 | 611.25 |
| 28DAP Chem Auto-self | 16 | 16 | | 8HV | 148.00 | 255.25 |
| 28DAP Chem Auto-self | 16 | 16 | | 8LV | 325.75 | 513.25 |
| Untreated Hand Polinated | | 0 | D | UHP | 263.00 | 263.00 |
| 14DAP Chem Auto-self | 6 | 6 | | 3HV | 616.75 | 766.25 |
| 14DAP Chem Auto-self | 6 | 6 | | 3LV | 631.25 | 839.25 |
| 28DAP Chem Auto-self | 16 | 16 | | 8HV | 581.75 | 646.75 |
| 28DAP Chem Auto-self | 16 | 16 | | 8LV | 727.75 | 745.50 |
| Untreated Hand Polinated | | 0 | E | UHP | 325.50 | 325.50 |
| 14DAP Chem Auto-self | 6 | 6 | | 3HV | 334.50 | 405.25 |
| 14DAP Chem Auto-self | 6 | 6 | | 3LV | 291.25 | 422.50 |
| 28DAP Chem Auto-self | 16 | 16 | | 8HV | 532.50 | 678.25 |
| 28DAP Chem Auto-self | 16 | 16 | | 8LV | 583.25 | 772.75 |
| Untreated Hand Polinated | | 0 | F | UHP | 109.00 | 109.00 |
| 14DAP Chem Auto-self | 6 | 6 | | 3HV | 414.75 | 1078.75 |
| 14DAP Chem Auto-self | 6 | 6 | | 3LV | 392.00 | 777.75 |
| 28DAP Chem Auto-self | 16 | 16 | | 8HV | 301.00 | 442.25 |
| 28DAP Chem Auto-self | 16 | 16 | | 8LV | 461.00 | 661.00 |
| Untreated Hand Polinated | | 0 | G | UHP | 687.00 | 687.00 |
| 14DAP Chem Auto-self | 6 | 6 | | 3HV | 381.50 | 905.50 |
| 14DAP Chem Auto-self | 6 | 6 | | 3LV | 485.50 | 1033.50 |
| 28DAP Chem Auto-self | 16 | 16 | | 8HV | 284.50 | 567.00 |
| 28DAP Chem Auto-self | 16 | 16 | | 8LV | 542.75 | 728.25 |
| Untreated Hand Polinated | | 0 | H | UHP | 278.75 | 278.75 |
| 14DAP Chem Auto-self | 6 | 6 | | 3HV | 77.50 | 80.00 |
| 14DAP Chem Auto-self | 6 | 6 | | 3LV | 73.25 | 83.00 |
| 28DAP Chem Auto-self | 16 | 16 | | 8HV | 388.50 | 520.00 |
| 28DAP Chem Auto-self | 16 | 16 | | 8LV | 439.75 | 564.75 |
| Untreated Hand Polinated | | 0 | I | UHP | 264.75 | 264.75 |
| 14DAP Chem Auto-self | 10 | 10 | | 3HV | 172.00 | 218.75 |
| 14DAP Chem Auto-self | 10 | 10 | | 3LV | 175.00 | 191.25 |
| 28DAP Chem Auto-self | 32 | 32 | | 8HV | 508.75 | 550.50 |
| 28DAP Chem Auto-self | 32 | 32 | | 8LV | 448.25 | 448.25 |
| Untreated Hand Polinated | | 0 | J | UHP | 0.00 | 0.00 |
| 14DAP Chem Auto-self | 10 | 10 | | 3HV | 587.00 | 1005.75 |
| 14DAP Chem Auto-self | 10 | 10 | | 3LV | 602.75 | 953.25 |
| 28DAP Chem Auto-self | 32 | 32 | | 8HV | 361.50 | 398.75 |
| 28DAP Chem Auto-self | 32 | 32 | | 8LV | 280.50 | 298.75 |
| Untreated Hand Polinated | | 0 | K | UHP | 466.00 | 466.00 |

TABLE 10-continued

Average number of kernels from the main stem and total number of kernels per plant (including tillers).

| Treatment | PBCZ mg/plant | Active Ingredient Paclobutrazol mg/plant (0.12 g ai per fluid oz or 4000 ppm) | Pedigree | Treatment Code | Avg Kernels from Main Stem | Avg Total Kernels Per Plant |
|---|---|---|---|---|---|---|
| 14DAP Chem Auto-self | 6 | 6 | | 3HV | 317.75 | 365.00 |
| 14DAP Chem Auto-self | 6 | 6 | | K3LV | 418.75 | 437.75 |
| 28DAP Chem Auto-self | 16 | 16 | | 8HV | 446.75 | 487.00 |
| 28DAP Chem Auto-self | 16 | 16 | | 8LV | 495.00 | 539.75 |

Figure 10:
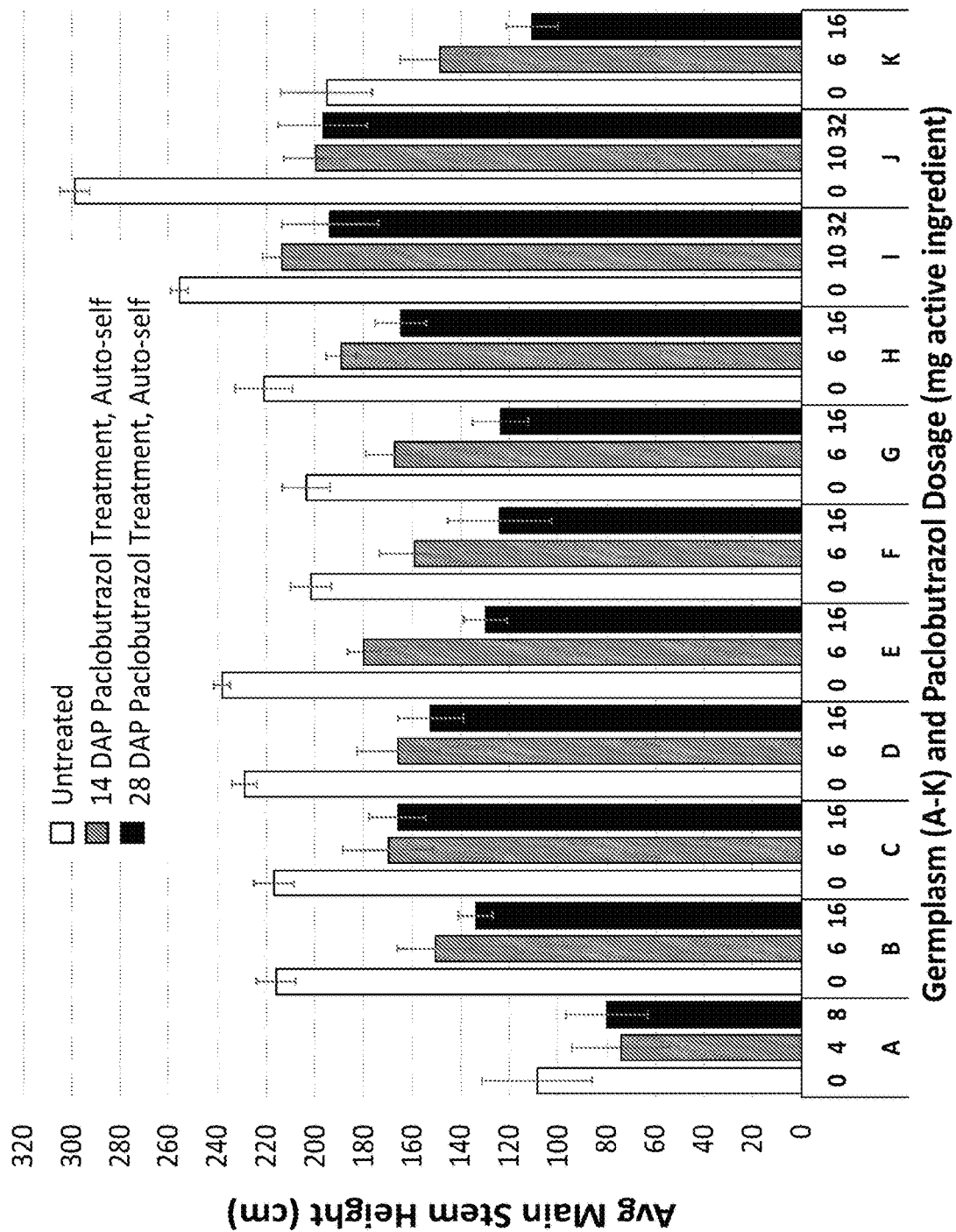
FIG. 10 shows the average main stem height (cm) in untreated or treated germplasm at 14 days after transplant or 28 day after transplant across unique germplasms (A-K).
Figure 11:
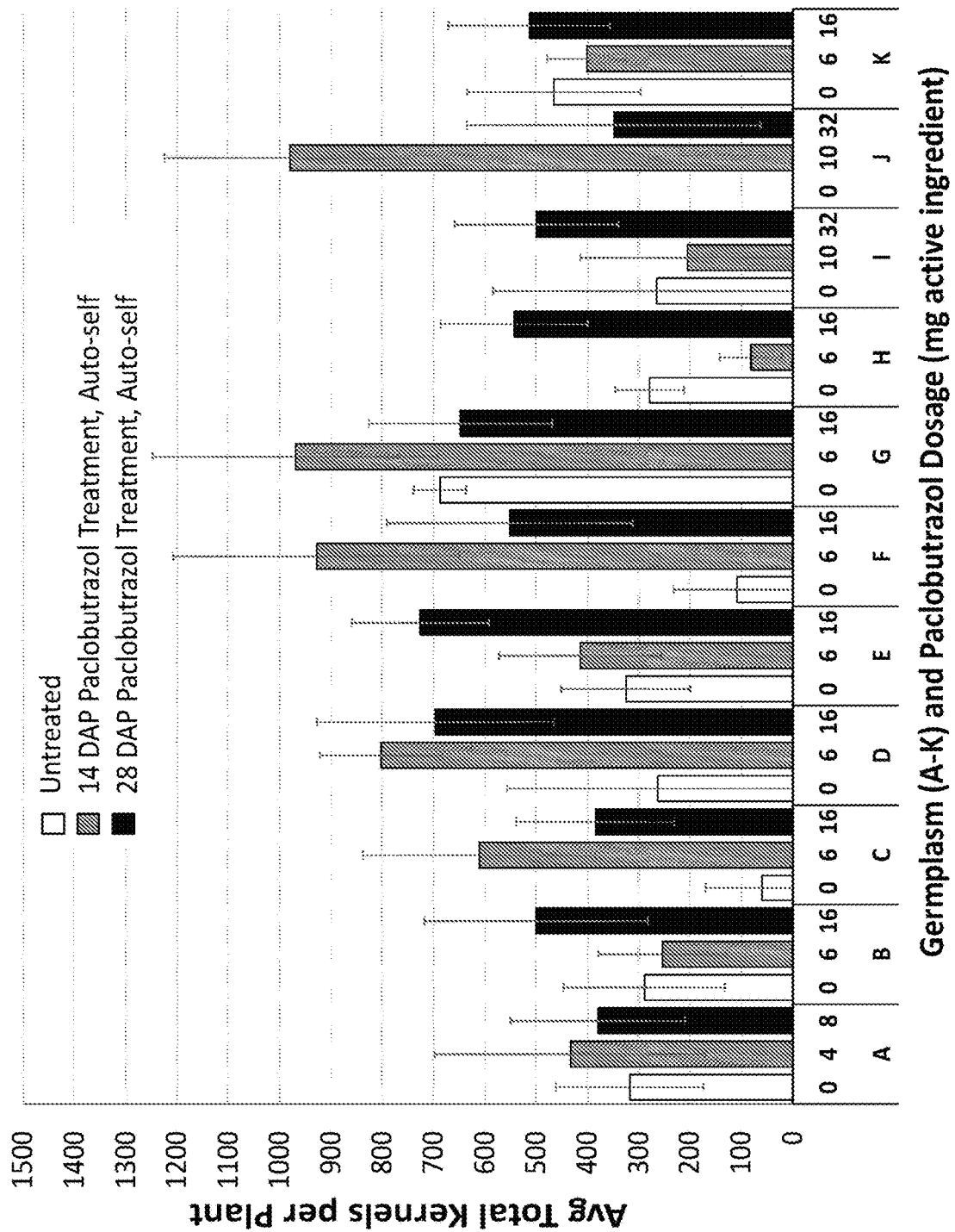
FIG. 11 shows the average kernels per plant per treatment across unique germplasms (A-K).

The chemistry treatment was highly penetrant throughout every germplasm tested. On average a decrease in height of about 30-50% was observed when the plants were treated with Paclobutrazol (FIG. 10). This enables whole plant bagging and closer proximity between silk and tassel. Furthermore, chemistry treatment of diverse germplasm at the V3 (14DAP) or V8 (28DAP) stages led to an average increase in kernel number per plant (FIG. 11).

Example 13. Manipulation of Corn Kernel Yield Using a Different Triazole Chemistry The following example describes chemistry manipulation of corn plants using one rate of Sumagic (active ingredient 0.055% Uniconazole; Valent USA) applied to the roots of the developing seedling.

Figure 9A:
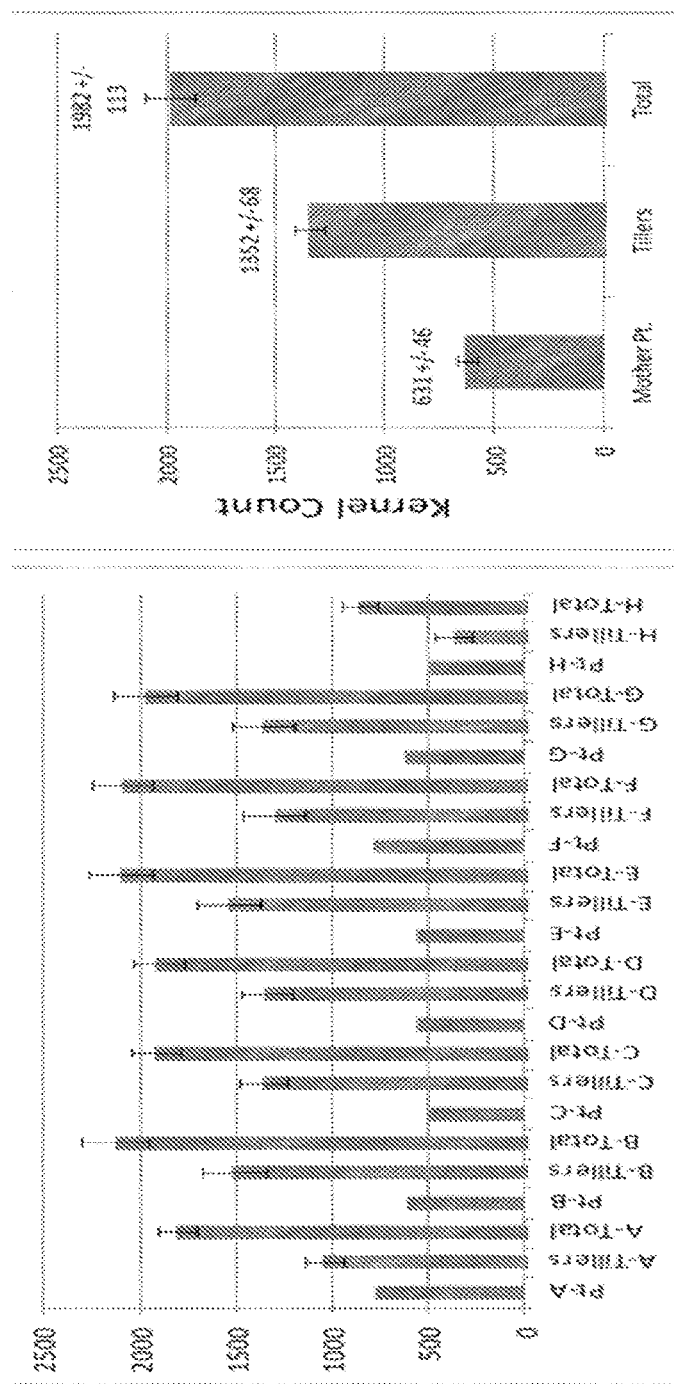
FIGS. 9A and B show kernels per plant counts of main stem ("Mothers"), tillers and total using A open pollinated or B hand pollinated methods.
Figure 9B:
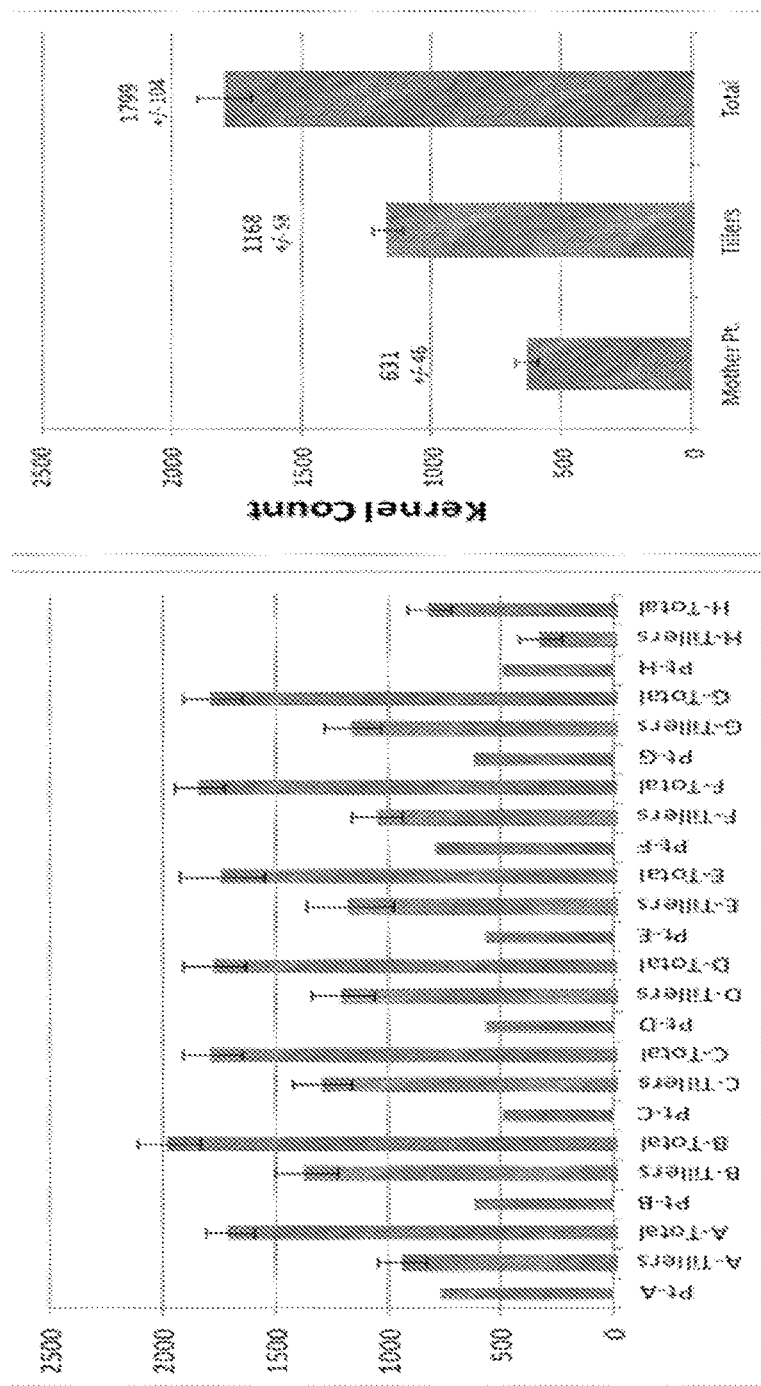

Corn seedlings were planted in six-packs as described in Example 1 and treated at the V3-stage (approximately 14 days post germination) with a 400 mL solution of 0.5% Sumagic. The six-pack was drenched directly in a bucket enclosure containing the chemistry to be applied. Approximately twelve days after the application, the first set of tillers were transplanted from the mother plant. There were eight plants total and four tillers transplanted per main stem. A total of thirty six tillers were transplanted. After the transplanted tillers had become established (V7-stage) they were treated an additional time with 0.5% Sumagic. Plants were then monitored throughout their growth cycle. Pollinations were carried out using standard methodology of hand pollinating between tassels and ears on the same plant. In some instances plants were open pollinated. At the completion of the experiment the number of kernels per plant (main stem or "mother" and combined four tillers removed per mother plant) were counted. FIG. 9A-B illustrates the results which show that on average the combination of main stem plus tillers produced through using a triazole chemistry induction can yield between 1700-2000 kernels per corn pedigree.

Example 14. Manipulation of Kernels Per Plant in Doubled Haploid Populations Using the Plant Growth Regulator Paclobutrazol Doubled Haploid seedlings were planted into soil one day after being treated with the haploid doubling agent colchicine and a total of seven days after germination. Plants of four different germplasm were treated with Paczol (2.5% in 60 mL equivalent to 0.4% active ingredient Paclobutrazol) at approximately 37 days after seed imbibition (approximately V11 stage) to form multiple co-dominant ears. All of the plants were hand pollinated for two consecutive days. Plants with co-dominant ears were hand pollinated on two separate ears on each plant (both primary and secondary ears were on the main stem). At the completion of the experiment total kernel number was determined per plant. Table 11 below illustrates the results of untreated and treated plants in each germplasm population.

TABLE 11

Paczol treatment of Dihaploid Germplasm Populations.

| Corn DH Germplasm | Number of plants treated or untreated | Average number of kernels per plant |
|---|---|---|
| Unique Germplasm #1 | Treated, 56 | 102 |
| Unique Germplasm #1 | Not-treated, 44 | 59 |
| Unique Germplasm #2 | Treated, 56 | 63 |
| Unique Germplasm #2 | Not-treated, 44 | 35 |
| Unique Germplasm #3 | Treated, 56 | 48 |
| Unique Germplasm #3 | Not-treated, 44 | 27 |
| Unique Germplasm #4 | Treated, 56 | 49 |
| Unique Germplasm #4 | Not-treated, 44 | 28 |
| Overall counts | Treated, 224 | 66 |
| | Not-treated, 176 | 37 |

Figure 13:
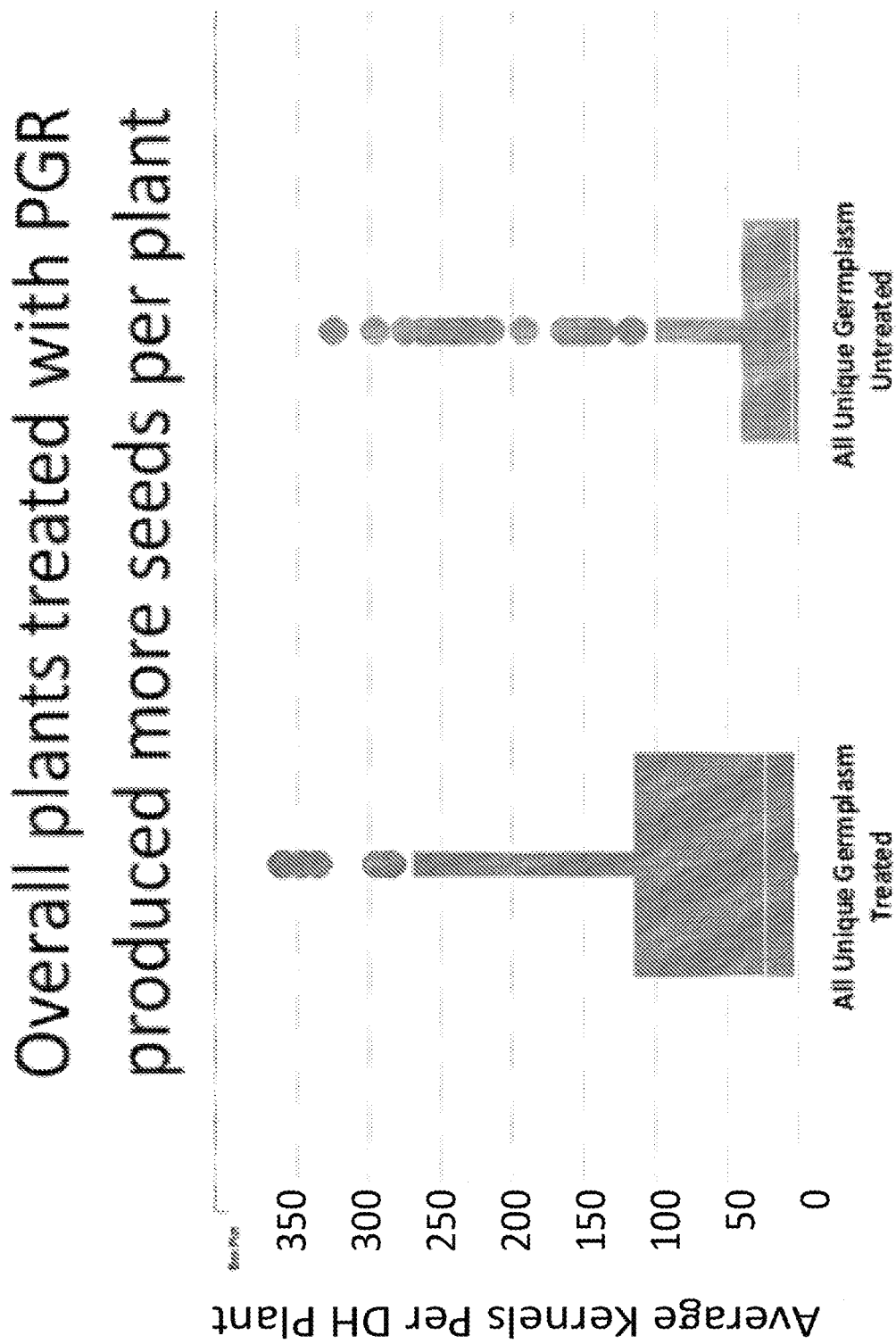
FIG. 13 shows that plants treated with GA-inhibitor produced more seeds per plant.
Figure 14:
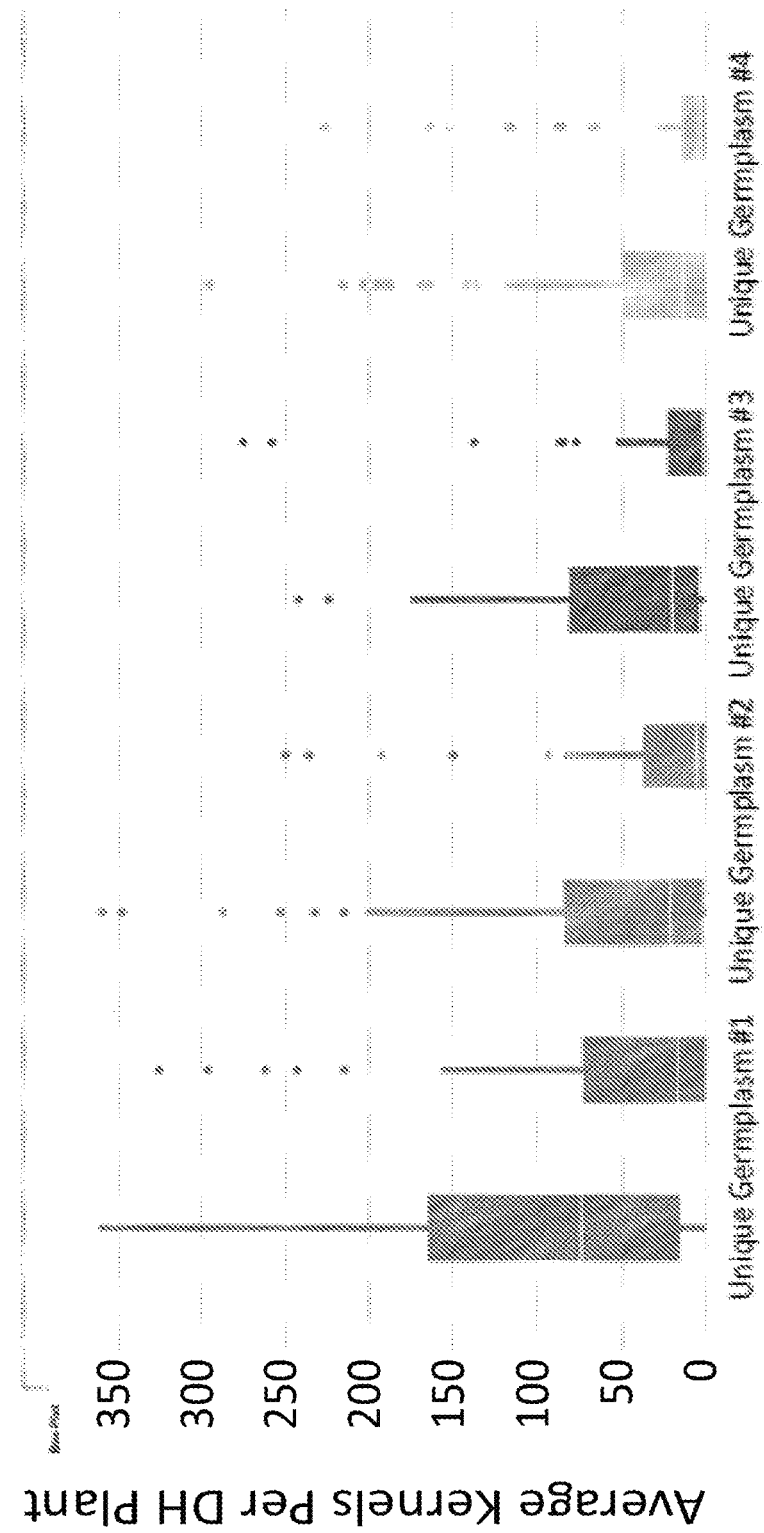
FIG. 14 shows that across lines, GA-inhibitor-treated plants produced more seeds per plant.

The number of kernels per plant was nearly doubled upon treatment with Paczol. See FIGS. 13 and 14.

Having illustrated and described the principles of these methods, it should be apparent to persons skilled in the art that the methods can be modified in arrangement and detail without departing from such principles. As various modifications could be made in the constructions herein described and illustrated without departing from the scope of the invention, it is intended that all matter contained in the foregoing description or shown in the accompanying drawings shall be interpreted as illustrative rather than limiting.

Although the materials and methods disclosed herein are described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

The breadth and scope of the present disclosure should not be limited by any of the above-described exemplary embodiments, but should be defined only in accordance with the following claims and their equivalents.

What is claimed is:

1. A method of treating a maize plant with a gibberellic acid-inhibitor (GA-inhibitor),
the method comprising administering the GA-inhibitor to the plant by contacting the plant with the GA-inhibitor, wherein the GA-inhibitor is administered at a rate of at least 1.0 mg/plant, prior to the formation of a visible reproductive structure,
wherein the treatment comprises at least one administration of the GA-inhibitor at the V6, V7, V8, or V9 stage to induce co-dominant ears on the main stem,
wherein the treatment increases seed yield of the maize plant as compared to an untreated control plant, and
wherein the treatment results in at least about 600 seed from the treated plant.

2. The method of claim 1, wherein the GA-inhibitor is administered by contacting the roots of the plant.

3. The method of claim 1, wherein the treatment reduces plant height.

4. The method of claim 1, wherein the plant is an inbred or a hybrid plant.

5. The method of claim 1, wherein the GA-inhibitor is a triazole.

6. The method of claim 5, wherein the triazole is selected from the group consisting of paclobutrazol, uniconazole, and flurprimidol.

7. The method of claim 1, wherein the GA-inhibitor is administered at a rate of about 1.0 mg/plant to about 75 mg/plant.

8. The method of claim 1, wherein the GA-inhibitor is administered at a rate of about 8.0 mg/plant to about 75 mg/plant.

9. The method of 1, wherein the treatment results in 1, 2, 3, 4, 5, 6, or 7 tillers on the treated plant.

10. The method of claim 9, wherein the tillers have delayed feminization and increased maleness.

11. The method of claim 1, wherein treatment with the GA-inhibitor increases pollen shed duration.

12. The method of claim 1, wherein the GA-inhibitor treated plant produces at least 1, 2, 3, 4, or 5, or more tillers than a control plant which was not contacted with the GA-inhibitor.

13. The method of claim 1, further comprising harvesting the seed of the treated maize plant.

14. The method of claim 13, further comprising genotyping a harvested seed or a population of harvested seeds.

15. The method of claim 13, further comprising using a harvested seed or a population of harvested seeds in a breeding program.

16. The method of claim 1, wherein the treated plant is grown under controlled conditions.

17. The method of claim 16, wherein the treated plant is grown in a green house.

18. The method of claim 1, wherein the treated plant is grown in an open field.

19. The method of claim 1, wherein a population of commercially planted plants is treated and wherein said treatment increases yield in comparison to a population of untreated control plants.

20. The method of claim 1, wherein the GA-inhibitor is administered at a rate of about 1.0 mg/plant to about 50 mg/plant.

21. The method of claim 1, wherein the GA-inhibitor is administered at a rate of from about 1.0 mg/plant to about 32 mg/plant.

22. The method of claim 1, wherein the GA-inhibitor is administered at a rate of about 8.0 mg/plant to about 50 mg/plant.

* * * * *